US012369975B2

(12) United States Patent
Govari et al.

(10) Patent No.: US 12,369,975 B2
(45) Date of Patent: Jul. 29, 2025

(54) BALLOON CATHETER WITH FORCE SENSOR

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 612 days.

(21) Appl. No.: 16/863,815

(22) Filed: Apr. 30, 2020

(65) Prior Publication Data

US 2021/0077180 A1 Mar. 18, 2021

Related U.S. Application Data

(60) Provisional application No. 62/899,259, filed on Sep. 12, 2019.

(51) Int. Cl.
*A61B 18/14* (2006.01)
*A61B 17/00* (2006.01)
(Continued)

(52) U.S. Cl.
CPC ......... *A61B 18/1492* (2013.01); *A61M 25/10* (2013.01); *A61B 2017/00199* (2013.01);
(Continued)

(58) Field of Classification Search
CPC ................ A61B 18/1492; A61B 34/20; A61B 2017/00199; A61B 2018/0022;
(Continued)

(56) References Cited

U.S. PATENT DOCUMENTS

D123,782 S 12/1940 Paul
3,316,896 A 5/1967 Louis
(Continued)

FOREIGN PATENT DOCUMENTS

CA 2285342 A1 4/1997
CN 101422637 A 5/2009
(Continued)

OTHER PUBLICATIONS

Partial European Search Report dated Feb. 16, 2021, from corresponding European Application No. 20195644.8.
(Continued)

*Primary Examiner* — Thomas A Giuliani
*Assistant Examiner* — Abigail M Ziegler

(57) ABSTRACT

In one embodiment, a system includes a balloon catheter configured to be inserted into a body-part of a living subject, the balloon catheter comprising an insertion tube having a distal tip, a force sensor connected to the distal tip, and an inflatable balloon including a proximal portion connected to the force sensor so that the force sensor is disposed between the distal tip of the insertion tube and the inflatable balloon, and multiple electrodes disposed around an outer surface of the balloon, and configured, when the balloon is inflated, to contact tissue at respective locations in the body-part, wherein the force sensor is configured to output at least one force signal indicative of a magnitude and a direction of a force applied by the balloon on the tissue when the balloon is inflated.

19 Claims, 17 Drawing Sheets

(51) Int. Cl.
*A61M 25/10* (2013.01)
*A61B 18/00* (2006.01)

(52) U.S. Cl.
CPC .......... *A61B 2018/0022* (2013.01); *A61B 2018/00351* (2013.01); *A61B 2018/00577* (2013.01); *A61B 2018/00797* (2013.01); *A61B 2018/00875* (2013.01); *A61B 2018/1467* (2013.01); *A61B 2218/002* (2013.01)

(58) Field of Classification Search
CPC .......... A61B 2018/00577; A61B 2018/00839; A61B 2018/1467; A61B 2018/00773; A61B 2034/2051; A61B 2560/0462; A61B 2090/065; A61M 25/10; A61M 2039/1033
See application file for complete search history.

(56) References Cited

U.S. PATENT DOCUMENTS

| | | | |
|---|---|---|---|
| 4,276,874 A | 7/1981 | Wolvek et al. | |
| 4,587,975 A | 5/1986 | Salo et al. | |
| 4,709,698 A | 12/1987 | Johnston et al. | |
| 4,744,366 A | 5/1988 | Jang | |
| 4,805,621 A | 2/1989 | Heinze et al. | |
| 5,078,714 A | 1/1992 | Katims | |
| 5,178,957 A | 1/1993 | Kolpe et al. | |
| 5,341,807 A | 8/1994 | Nardella | |
| 5,429,617 A | 7/1995 | Hammersmark et al. | |
| 5,447,529 A | 9/1995 | Marchlinski et al. | |
| 5,469,857 A | 11/1995 | Laurent et al. | |
| 5,496,311 A | 3/1996 | Abele et al. | |
| 5,582,609 A | 12/1996 | Swanson et al. | |
| 5,584,830 A | 12/1996 | Ladd et al. | |
| 5,662,108 A | 9/1997 | Budd et al. | |
| 5,673,704 A | 10/1997 | Marchlinski et al. | |
| 5,702,386 A | 12/1997 | Stern et al. | |
| 5,718,241 A | 2/1998 | Ben-Haim et al. | |
| 5,797,903 A | 8/1998 | Swanson et al. | |
| 5,836,874 A | 11/1998 | Swanson et al. | |
| 5,836,990 A | 11/1998 | Li | |
| 5,860,974 A | 1/1999 | Abele | |
| 5,891,095 A | 4/1999 | Eggers et al. | |
| 5,935,079 A | 8/1999 | Swanson et al. | |
| 5,971,983 A | 10/1999 | Lesh | |
| 6,012,457 A | 1/2000 | Lesh | |
| 6,024,740 A | 2/2000 | Lesh et al. | |
| 6,042,580 A | 3/2000 | Simpson | |
| 6,123,718 A | 9/2000 | Tu et al. | |
| 6,164,283 A | 12/2000 | Lesh | |
| 6,171,275 B1 | 1/2001 | Webster, Jr. | |
| 6,176,832 B1 | 1/2001 | Habu et al. | |
| 6,198,974 B1 | 3/2001 | Webster, Jr. | |
| 6,226,542 B1 | 5/2001 | Reisfeld | |
| 6,241,724 B1 | 6/2001 | Fleischman et al. | |
| 6,301,496 B1 | 10/2001 | Reisfeld | |
| 6,322,558 B1 | 11/2001 | Taylor et al. | |
| 6,380,957 B1 | 4/2002 | Banning | |
| 6,402,740 B1 | 6/2002 | Ellis et al. | |
| D462,389 S | 9/2002 | Provence et al. | |
| 6,471,693 B1 | 10/2002 | Carroll et al. | |
| 6,522,930 B1 | 2/2003 | Schaer et al. | |
| 6,656,174 B1 | 12/2003 | Hegde et al. | |
| 6,695,808 B2 | 2/2004 | Tom | |
| 6,814,733 B2 | 11/2004 | Schwartz et al. | |
| 6,892,091 B1 | 5/2005 | Ben-Haim et al. | |
| 6,893,433 B2 | 5/2005 | Lentz | |
| 6,915,149 B2 | 7/2005 | Ben-Haim | |
| 6,986,744 B1 | 1/2006 | Krivitski | |
| 6,987,995 B2 | 1/2006 | Drysen | |
| 6,997,924 B2 | 2/2006 | Schwartz et al. | |
| 7,142,903 B2 | 11/2006 | Rodriguez et al. | |
| 7,156,816 B2 | 1/2007 | Schwartz et al. | |
| 7,274,957 B2 | 9/2007 | Drysen | |
| 7,340,307 B2 | 3/2008 | Maguire et al. | |
| 7,377,906 B2 | 5/2008 | Selkee | |
| 7,442,190 B2 | 10/2008 | Abbound et al. | |
| 7,536,218 B2 | 5/2009 | Govari et al. | |
| 7,591,799 B2 | 9/2009 | Selkee | |
| 7,593,760 B2 | 9/2009 | Rodriguez et al. | |
| 7,720,517 B2 | 5/2010 | Drysen | |
| 7,756,576 B2 | 7/2010 | Levin | |
| 7,842,031 B2 | 11/2010 | Abboud et al. | |
| 7,853,302 B2 | 12/2010 | Rodriguez et al. | |
| 8,000,765 B2 | 8/2011 | Rodriguez et al. | |
| 8,021,327 B2 | 9/2011 | Selkee | |
| 8,048,032 B2 | 11/2011 | Root et al. | |
| 8,231,617 B2 | 7/2012 | Satake | |
| 8,267,932 B2 | 9/2012 | Baxter et al. | |
| 8,275,440 B2 | 9/2012 | Rodriguez et al. | |
| 8,348,888 B2 | 1/2013 | Selkee | |
| 8,357,152 B2 | 1/2013 | Govari et al. | |
| D682,289 S | 5/2013 | DiJulio et al. | |
| D682,291 S | 5/2013 | Baek et al. | |
| D690,318 S | 9/2013 | Kluttz et al. | |
| D694,652 S | 12/2013 | Tompkin | |
| 8,641,709 B2 | 2/2014 | Sauvageau et al. | |
| 8,721,590 B2 | 5/2014 | Seward et al. | |
| 8,777,161 B2 | 7/2014 | Pollock et al. | |
| D716,340 S | 10/2014 | Bresin et al. | |
| 8,852,181 B2 | 10/2014 | Malecki et al. | |
| D720,766 S | 1/2015 | Mandal et al. | |
| D721,379 S | 1/2015 | Moon et al. | |
| D724,618 S | 3/2015 | Shin | |
| 8,998,893 B2 | 4/2015 | Avitall | |
| D729,263 S | 5/2015 | Ahn et al. | |
| 9,050,105 B2 * | 6/2015 | Govari | A61B 18/1492 |
| 9,089,350 B2 | 7/2015 | Willard | |
| D736,780 S | 8/2015 | Wang | |
| 9,126,023 B1 | 9/2015 | Sahatjian et al. | |
| D740,308 S | 10/2015 | Kim et al. | |
| 9,168,004 B2 | 10/2015 | Gliner et al. | |
| D743,424 S | 11/2015 | Danielyan et al. | |
| D744,000 S | 11/2015 | Villamor et al. | |
| 9,173,758 B2 | 11/2015 | Brister et al. | |
| D747,742 S | 1/2016 | Fan et al. | |
| D750,644 S | 3/2016 | Bhutani et al. | |
| 9,283,034 B2 | 3/2016 | Katoh et al. | |
| 9,289,141 B2 | 3/2016 | Lowery et al. | |
| D753,690 S | 4/2016 | Vazquez et al. | |
| 9,320,631 B2 | 4/2016 | Moore et al. | |
| 9,345,540 B2 | 5/2016 | Mallin et al. | |
| D759,673 S | 6/2016 | Looney et al. | |
| D759,675 S | 6/2016 | Looney et al. | |
| D764,500 S | 8/2016 | Wang | |
| D765,709 S | 9/2016 | Gagnier | |
| D767,616 S | 9/2016 | Jones et al. | |
| D768,696 S | 10/2016 | Gagnier | |
| D783,037 S | 4/2017 | Hariharan et al. | |
| 9,655,677 B2 | 5/2017 | Salahieh et al. | |
| D791,805 S | 7/2017 | Segars | |
| 9,795,442 B2 | 10/2017 | Salahieh et al. | |
| 9,907,610 B2 | 3/2018 | Beeckler et al. | |
| 9,956,035 B2 | 5/2018 | Govari et al. | |
| 10,349,824 B2 | 7/2019 | Claude et al. | |
| D861,717 S | 10/2019 | Brekke et al. | |
| 10,688,278 B2 | 6/2020 | Beeckler et al. | |
| 2001/0031961 A1 | 10/2001 | Hooven | |
| 2002/0002369 A1 | 1/2002 | Hood | |
| 2002/0065455 A1 | 5/2002 | Ben-Haim et al. | |
| 2002/0068931 A1 | 6/2002 | Wong et al. | |
| 2002/0077627 A1 | 6/2002 | Johnson et al. | |
| 2002/0160134 A1 | 10/2002 | Ogushi et al. | |
| 2003/0018327 A1 | 1/2003 | Truckai et al. | |
| 2003/0028183 A1 | 2/2003 | Sanchez et al. | |
| 2003/0050637 A1 | 3/2003 | Maguire et al. | |
| 2003/0060820 A1 | 3/2003 | Maguire et al. | |
| 2003/0144658 A1 | 7/2003 | Schwartz et al. | |
| 2004/0122445 A1 | 6/2004 | Butler et al. | |
| 2004/0147920 A1 | 7/2004 | Keidar | |
| 2004/0225285 A1 | 11/2004 | Gibson | |
| 2005/0070887 A1 | 3/2005 | Taimisto et al. | |
| 2005/0119686 A1 | 6/2005 | Clubb | |
| 2005/0203597 A1 | 9/2005 | Yamazaki et al. | |

(56) References Cited

U.S. PATENT DOCUMENTS

| | | |
|---|---|---|
| 2006/0013595 A1 | 1/2006 | Trezza et al. |
| 2006/0106375 A1 | 5/2006 | Werneth et al. |
| 2006/0135953 A1 | 6/2006 | Kania et al. |
| 2007/0071792 A1 | 3/2007 | Varner et al. |
| 2007/0080322 A1 | 4/2007 | Walba |
| 2007/0083194 A1 | 4/2007 | Kunis et al. |
| 2007/0100332 A1 | 5/2007 | Paul et al. |
| 2007/0287994 A1 | 12/2007 | Patel |
| 2008/0018891 A1 | 1/2008 | Hell et al. |
| 2008/0021313 A1 | 1/2008 | Eidenschink et al. |
| 2008/0051707 A1 | 2/2008 | Phan et al. |
| 2008/0140072 A1 | 6/2008 | Stangenes et al. |
| 2008/0183132 A1 | 7/2008 | Davies et al. |
| 2008/0188912 A1 | 8/2008 | Stone et al. |
| 2008/0202637 A1 | 8/2008 | Hector et al. |
| 2008/0208186 A1 | 8/2008 | Slater |
| 2008/0249463 A1 | 10/2008 | Pappone et al. |
| 2008/0262489 A1 | 10/2008 | Steinke |
| 2008/0281312 A1 | 11/2008 | Werneth et al. |
| 2009/0093806 A1 | 4/2009 | Govari et al. |
| 2009/0163890 A1 | 6/2009 | Clifford et al. |
| 2009/0182318 A1 | 7/2009 | Abboud et al. |
| 2009/0270850 A1 | 10/2009 | Zhou et al. |
| 2010/0069836 A1 | 3/2010 | Satake |
| 2010/0114269 A1 | 5/2010 | Wittenberger et al. |
| 2010/0204560 A1 | 8/2010 | Salahieh et al. |
| 2010/0256629 A1 | 10/2010 | Wylie et al. |
| 2010/0324552 A1 | 12/2010 | Kauphusman et al. |
| 2011/0118632 A1 | 5/2011 | Sinelnikov et al. |
| 2011/0130648 A1 | 6/2011 | Beeckler et al. |
| 2011/0282338 A1 | 11/2011 | Fojtik |
| 2011/0295248 A1 | 12/2011 | Wallace et al. |
| 2011/0301587 A1 | 12/2011 | Deem et al. |
| 2011/0313286 A1 | 12/2011 | Whayne et al. |
| 2012/0010490 A1* | 1/2012 | Kauphusman ......... A61B 5/287 600/373 |
| 2012/0019107 A1 | 1/2012 | Gabl et al. |
| 2012/0029511 A1 | 2/2012 | Smith et al. |
| 2012/0065503 A1 | 3/2012 | Rogers et al. |
| 2012/0071870 A1 | 3/2012 | Salahieh et al. |
| 2012/0079427 A1 | 3/2012 | Carmichael et al. |
| 2012/0101413 A1 | 4/2012 | Beetel et al. |
| 2012/0101538 A1 | 4/2012 | Ballakur et al. |
| 2012/0143177 A1 | 6/2012 | Avitall |
| 2012/0143293 A1 | 6/2012 | Mauch et al. |
| 2012/0191079 A1 | 7/2012 | Moll et al. |
| 2012/0209260 A1 | 8/2012 | Lambert et al. |
| 2013/0085360 A1 | 4/2013 | Grunewald |
| 2013/0090649 A1 | 4/2013 | Smith et al. |
| 2013/0109982 A1 | 5/2013 | Sato et al. |
| 2013/0150693 A1 | 6/2013 | D'Angelo et al. |
| 2013/0165916 A1 | 6/2013 | Mathur et al. |
| 2013/0165941 A1 | 6/2013 | Murphy |
| 2013/0165990 A1 | 6/2013 | Mathur et al. |
| 2013/0169624 A1 | 7/2013 | Bourier et al. |
| 2013/0261692 A1 | 10/2013 | Cardinal et al. |
| 2013/0274562 A1 | 10/2013 | Ghaffari et al. |
| 2013/0274658 A1 | 10/2013 | Steinke et al. |
| 2013/0282084 A1 | 10/2013 | Mathur et al. |
| 2013/0318439 A1 | 11/2013 | Landis et al. |
| 2014/0012160 A1 | 1/2014 | Ghaffari et al. |
| 2014/0012242 A1 | 1/2014 | Lee et al. |
| 2014/0018788 A1 | 1/2014 | Engelman et al. |
| 2014/0031813 A1 | 1/2014 | Tellio et al. |
| 2014/0058197 A1 | 2/2014 | Salahieh et al. |
| 2014/0121470 A1 | 5/2014 | Scharf et al. |
| 2014/0148805 A1 | 5/2014 | Stewart et al. |
| 2014/0227437 A1 | 8/2014 | DeBoer et al. |
| 2014/0243821 A1 | 8/2014 | Salahieh et al. |
| 2014/0275993 A1 | 9/2014 | Ballakur |
| 2014/0276756 A1 | 9/2014 | Hill |
| 2014/0276811 A1 | 9/2014 | Koblish et al. |
| 2014/0288546 A1 | 9/2014 | Sherman et al. |
| 2014/0330266 A1 | 11/2014 | Thompson et al. |
| 2014/0357956 A1 | 12/2014 | Salahieh et al. |
| 2015/0005799 A1 | 1/2015 | Lindquist et al. |
| 2015/0025532 A1 | 1/2015 | Hanson et al. |
| 2015/0025533 A1 | 1/2015 | Groff et al. |
| 2015/0057655 A1 | 2/2015 | Osypka |
| 2015/0067512 A1 | 3/2015 | Roswell |
| 2015/0080883 A1 | 3/2015 | Haverkost et al. |
| 2015/0105774 A1 | 4/2015 | Lindquist et al. |
| 2015/0112256 A1 | 4/2015 | Byrne et al. |
| 2015/0112321 A1 | 4/2015 | Cadouri |
| 2015/0119875 A1 | 4/2015 | Fischell et al. |
| 2015/0141982 A1 | 5/2015 | Lee |
| 2015/0141987 A1 | 5/2015 | Caplan et al. |
| 2015/0157382 A1 | 6/2015 | Avitall et al. |
| 2015/0216591 A1 | 8/2015 | Cao et al. |
| 2015/0216650 A1 | 8/2015 | Shaltis |
| 2015/0265329 A1 | 9/2015 | Lalonde et al. |
| 2015/0265339 A1 | 9/2015 | Lindquist et al. |
| 2015/0265812 A1 | 9/2015 | Lalonde |
| 2015/0272667 A1 | 10/2015 | Govari et al. |
| 2015/0327805 A1 | 11/2015 | Ben-Haim |
| 2015/0341752 A1 | 11/2015 | Flynn |
| 2016/0000499 A1 | 1/2016 | Lennox et al. |
| 2016/0051321 A1 | 2/2016 | Salahieh et al. |
| 2016/0085431 A1 | 3/2016 | Kim et al. |
| 2016/0106499 A1 | 4/2016 | Ogata et al. |
| 2016/0166306 A1 | 6/2016 | Pageard |
| 2016/0175041 A1 | 6/2016 | Govari et al. |
| 2016/0196635 A1 | 7/2016 | Cho et al. |
| 2016/0256305 A1 | 9/2016 | Longo et al. |
| 2016/0374748 A9 | 12/2016 | Salahieh et al. |
| 2017/0042614 A1 | 2/2017 | Salahieh et al. |
| 2017/0042615 A1 | 2/2017 | Salahieh et al. |
| 2017/0080192 A1 | 3/2017 | Giasolli et al. |
| 2017/0143201 A1* | 5/2017 | Claude ..................... A61B 1/05 |
| 2017/0143359 A1 | 5/2017 | Nguyen et al. |
| 2017/0164464 A1 | 6/2017 | Weinkam et al. |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0347896 A1 | 12/2017 | Keyes et al. |
| 2018/0074693 A1 | 3/2018 | Jones et al. |
| 2018/0110562 A1 | 4/2018 | Govari et al. |
| 2018/0125382 A1* | 5/2018 | Govari ................... A61B 5/283 |
| 2018/0125575 A1 | 5/2018 | Schwartz et al. |
| 2018/0256247 A1* | 9/2018 | Govari ................... A61B 5/062 |
| 2018/0271590 A1* | 9/2018 | Basu ................. A61M 25/0043 |
| 2018/0280080 A1 | 10/2018 | Govari et al. |
| 2018/0333162 A1 | 11/2018 | Saab |
| 2018/0368927 A1 | 12/2018 | Lyons et al. |
| 2019/0059818 A1 | 2/2019 | Herrera et al. |
| 2019/0060622 A1 | 2/2019 | Beeckler |
| 2019/0143079 A1 | 5/2019 | Beeckler et al. |
| 2019/0175262 A1 | 6/2019 | Govari et al. |
| 2019/0175263 A1 | 6/2019 | Altmann et al. |
| 2019/0175265 A1 | 6/2019 | Altmann |
| 2019/0183567 A1 | 6/2019 | Govari et al. |
| 2019/0201669 A1 | 7/2019 | Govari et al. |
| 2019/0217065 A1 | 7/2019 | Govari et al. |
| 2019/0297441 A1 | 9/2019 | Dehe et al. |
| 2019/0298441 A1* | 10/2019 | Clark ................. A61B 18/1492 |
| 2019/0365451 A1 | 12/2019 | Jung, Jr. |
| 2020/0001054 A1 | 1/2020 | Jimenez et al. |
| 2020/0015693 A1 | 1/2020 | Beeckler et al. |
| 2020/0085497 A1 | 3/2020 | Zhang et al. |
| 2020/0107877 A1* | 4/2020 | Koblish ................... A61B 5/01 |
| 2020/0155226 A1 | 5/2020 | Valls et al. |
| 2021/0169567 A1 | 6/2021 | Govari et al. |

FOREIGN PATENT DOCUMENTS

| | | |
|---|---|---|
| CN | 102271607 A | 12/2011 |
| CN | 102458566 A | 5/2012 |
| CN | 203539434 U | 4/2014 |
| CN | 104244856 A | 12/2014 |
| CN | 104546117 A | 4/2015 |
| CN | 104644161 A | 5/2015 |
| CN | 105105844 A | 12/2015 |
| CN | 105473091 A | 4/2016 |
| CN | 105473093 A | 4/2016 |

(56) References Cited

FOREIGN PATENT DOCUMENTS

| | | | |
|---|---|---|---|
| CN | 106572842 A | 4/2017 | |
| CN | 109953813 A | 7/2019 | |
| CN | 110062607 A | 7/2019 | |
| EP | 0779059 A1 | 6/1997 | |
| EP | 1790304 A2 | 5/2007 | |
| EP | 2749214 A1 | 7/2014 | |
| EP | 2865350 A2 | 4/2015 | |
| EP | 2875790 A2 | 5/2015 | |
| EP | 3238646 A2 | 11/2017 | |
| EP | 3238648 A1 | 11/2017 | |
| EP | 3251622 A1 | 12/2017 | |
| EP | 3300680 A1 | 4/2018 | |
| EP | 3315087 A1 | 5/2018 | |
| EP | 3332727 A2 | 6/2018 | |
| EP | 3571983 A2 | 11/2019 | |
| EP | 3586778 A1 | 1/2020 | |
| EP | 3653153 A1 | 5/2020 | |
| JP | H06261951 A | 9/1994 | |
| JP | H1176233 A | 3/1999 | |
| JP | 2000504242 A | 4/2000 | |
| JP | 2005052424 A | 3/2005 | |
| JP | 2006212348 A | 8/2006 | |
| JP | 2010507404 A | 3/2010 | |
| JP | 2012024156 A | 2/2012 | |
| JP | 2013013726 A | 1/2013 | |
| JP | 2013078587 A | 5/2013 | |
| JP | 2013529109 A | 7/2013 | |
| JP | 2014529419 A | 11/2014 | |
| JP | 2015503365 A | 2/2015 | |
| JP | 2015100706 A | 6/2015 | |
| JP | 2015112113 A | 6/2015 | |
| JP | 2015112114 A | 6/2015 | |
| JP | 2015518776 A | 7/2015 | |
| JP | 2016515442 A | 5/2016 | |
| JP | 2016116863 A | 6/2016 | |
| JP | 2018524085 A | 8/2018 | |
| JP | 2018143771 A | 9/2018 | |
| JP | 2018161471 A | 10/2018 | |
| WO | 0056237 A2 | 9/2000 | |
| WO | 02102231 A2 | 12/2002 | |
| WO | 2005041748 A2 | 5/2005 | |
| WO | 2008049087 A2 | 4/2008 | |
| WO | 2011143468 A2 | 11/2011 | |
| WO | WO 2011/139589 A9 | 11/2011 | |
| WO | 2013049601 A2 | 4/2013 | |
| WO | 2013052919 A2 | 4/2013 | |
| WO | 2013154776 A2 | 10/2013 | |
| WO | 2014168987 A1 | 10/2014 | |
| WO | 2015049784 A1 | 4/2015 | |
| WO | 2016183337 A2 | 11/2016 | |
| WO | 2016210437 A1 | 12/2016 | |
| WO | 2017024306 A1 | 2/2017 | |
| WO | 2017087549 A1 | 5/2017 | |
| WO | 2018106569 A1 | 6/2018 | |
| WO | 2018129133 A1 | 7/2018 | |
| WO | 2019095020 A1 | 5/2019 | |

OTHER PUBLICATIONS

Extended European Search Report dated May 19, 2021, from corresponding European Application No. 20195644.8.
Angela O., "AF Symposium 2017: First-in-Man Study Shows Promising Results with a Multi-Electrode Radiofrequency Balloon for Paroxysmal AF Treatment," Cardiac Rhythm News, Jan. 20, 2017, 2 Pages, [Retrieved on Dec. 16, 2020] Retrieved from URL: https://cardiacrhythmnews.com/fist-in-man-study-shows-promising-results-with-a-multi-electrode-radiofrequency-balloon-for-paroxysmal-af-treatment/.
Casella M., et al., "Ablation Index as a Predictor of Long-Term Efficacy in Premature Ventricular Complex Ablation: A Regional Target Value Analysis," Heart Rhythm Society, Jun. 2019, vol. 16, No. 6, pp. 888-895.
Co-Pending U.S. Appl. No. 14/578,807, filed Dec. 22, 2014, 21 pages.

Das M., et al., "Ablation Index, a Novel Marker of Ablation Lesion Quality: Prediction of Pulmonary Vein Reconnection at Repeat Electrophysiology Study and Regional Differences in Target Values," Europace, 2017, Published Online May 31, 2016, vol. 19, pp. 775-783.
Dorobantu M., et al., "Oral Anticoagulation During Atrial Fibrillation Ablation: Facts and Controversies," Cor et Vasa, 2013, Accepted on Dec. 3, 2012, vol. 55, No. 2, pp. e101-e106, Retrieved from URL: https://www.sciencedirect.com/science/article/pii/S0010865012001415.
Extended European Search Report for Application No. EP17168513.4 mailed Sep. 18, 2017, 11 pages.
Extended European Search Report for European Application No. 15201723.2, mailed May 11, 2016, 07 Pages.
Extended European Search Report for European Application No. 17168393.1 mailed Dec. 15, 2017, 12 Pages.
Extended European Search Report for European Application No. 17168518.3, mailed Sep. 20, 2017, 9 Pages.
Extended European Search Report for European Application No. 17173893.3, mailed Nov. 6, 2017, 8 Pages.
Extended European Search Report for European Application No. 17201434.2, mailed Feb. 1, 2018, 10 Pages.
Extended European Search Report for European Application No. 17205876.0, mailed Jun. 1, 2018, 13 Pages.
Extended European Search Report for European Application No. 19177365.4, mailed Nov. 8, 2019, 07 Pages.
Extended European Search Report for European Application No. 19183327.6, mailed Nov. 21, 2019, 8 Pages.
Extended European Search Report for European Application No. 20153872.5, mailed May 7, 2020, 9 Pages.
Extended European Search Report for European Application No. 20195648.9, mailed Feb. 12, 2021, 8 Pages.
Fornell D., "Multi-Electrode RF Balloon Efficient for Acute Pulmonary Vein Isolation," Diagnostic and Interventional Cardiology, May 17, 2017, 3 Pages, [Retrieved on Dec. 16, 2020] Retrieved from URL: www.dicardiology.com/article/multi-electrode-rf-balloon-efficient-acute-pulmonary-vein-isolation.
Haines D.E., et al., "The Promise of Pulsed Field Ablation," Dec. 2019, vol. 19, No. 12, 10 pages.
Honarbakhsh S., et al., "Radiofrequency Balloon Catheter Ablation for Paroxysmal Atrial Fibrillation, Radiance Study—a UK experience," EP Europace, Oct. 2017, vol. 19, No. 1, p. i21, 3 Pages.
International Search Report and Written Opinion for International Application No. PCT/IB2019/052313, mailed Jul. 22, 2019, 8 Pages.
International Search Report and Written Opinion for International Application No. PCT/IB2019/056381, mailed Dec. 17, 2019, 10 pages.
International Search Report and Written Opinion for International Application No. PCT/IB2019/057743, mailed Dec. 6, 2019, 16 Pages.
International Search Report and Written Opinion issued in corresponding International Application No. PCT/IB2019/057742, dated Nov. 28, 2019, 18 Pages.
Nagashima K., et al., "Hot Balloon Versus Cryoballoon Ablation for Atrial Fibrillation," Circulation: Arrhythmia and Electrophysiology, May 2018, vol. 11, No. 5, e005861, 9 Pages.
Napoli N., et al., "For Atrial Fibrillation Ablation, Newer Anticoagulant Reduces Major Bleeds," American College of Cardiology, Mar. 19, 2017, 4 Pages, [Retrieved on Jan. 21, 2022] Retrieved from URL: https://www.acc.org/about-acc/press-releases/2017/03/18/08/47/sun-1045am-for-atrial-fibrillation-ablation-newer-anticoagulant-reduces-major-bleeds.
Okano T., et al., "Wire Perforation Causing Cardiopulmonary Arrest During Radiofrequency Hot Balloon Ablation for Pulmonary Vein Isolation," Journal of Cardiology Cases, Feb. 15, 2019, vol. 19, No. 5, pp. 169-172.
Partial European Search Report for European Application No. 17168393.1 mailed Sep. 13, 2017, 13 Pages.
Partial European Search Report for European Application No. 17205876.0, mailed Feb. 22, 2018, 10 Pages.

(56) References Cited

OTHER PUBLICATIONS

Reddy V.Y., et al., "Balloon Catheter Ablation to Treat Paroxysmal Atrial Fibrillation: What is the Level of Pulmonary Venous Isolation?," Heart Rhythm, Mar. 2008, vol. 5, No. 3, pp. 353-360, 3 Pages.
Winkle R.A., et al., "Atrial Fibrillation Ablation Using Open-Irrigated Tip Radiofrequency: Experience with Intraprocedural Activated Clotting Times ≤ 210 Seconds," Heart Rhythm, Jun. 2014, Epub Mar. 27, 2014, vol. 11, No. 6, pp. 963-968.
Youtube:, "Intensity™ CX4 Professional E-Stim/ Ultrasound Combo," Dec. 22, 2015, 1 Page, [Retrieved on Nov. 19, 2020], Retrieved from URL: https://www.youtube.com/watch?v=76s1QkMWJME].
Youtube: "New Interface TactiCath Contact Force Ablation Catheter," Nov. 26, 2013, 1 Pages, [Retrieved on Nov. 19, 2020], Retrieved from URL: https: /Avww.youtube.com/watch?v=aYvYO8Hpylg].
Notice of Reasons for Refusal with English translation dated May 7, 2024, from corresponding Japanese Application No. JP2020152783.
Notice of Reasons for Refusal with English translation dated Oct. 1, 2024, from corresponding Japanese Application No. JP2020152783.
First Search dated Mar. 6, 2025, from corresponding Chinese Application No. 202010952827.8.
First Office Action dated Mar. 6, 2025, from corresponding Chinese Application No. 202010952827.8.

\* cited by examiner

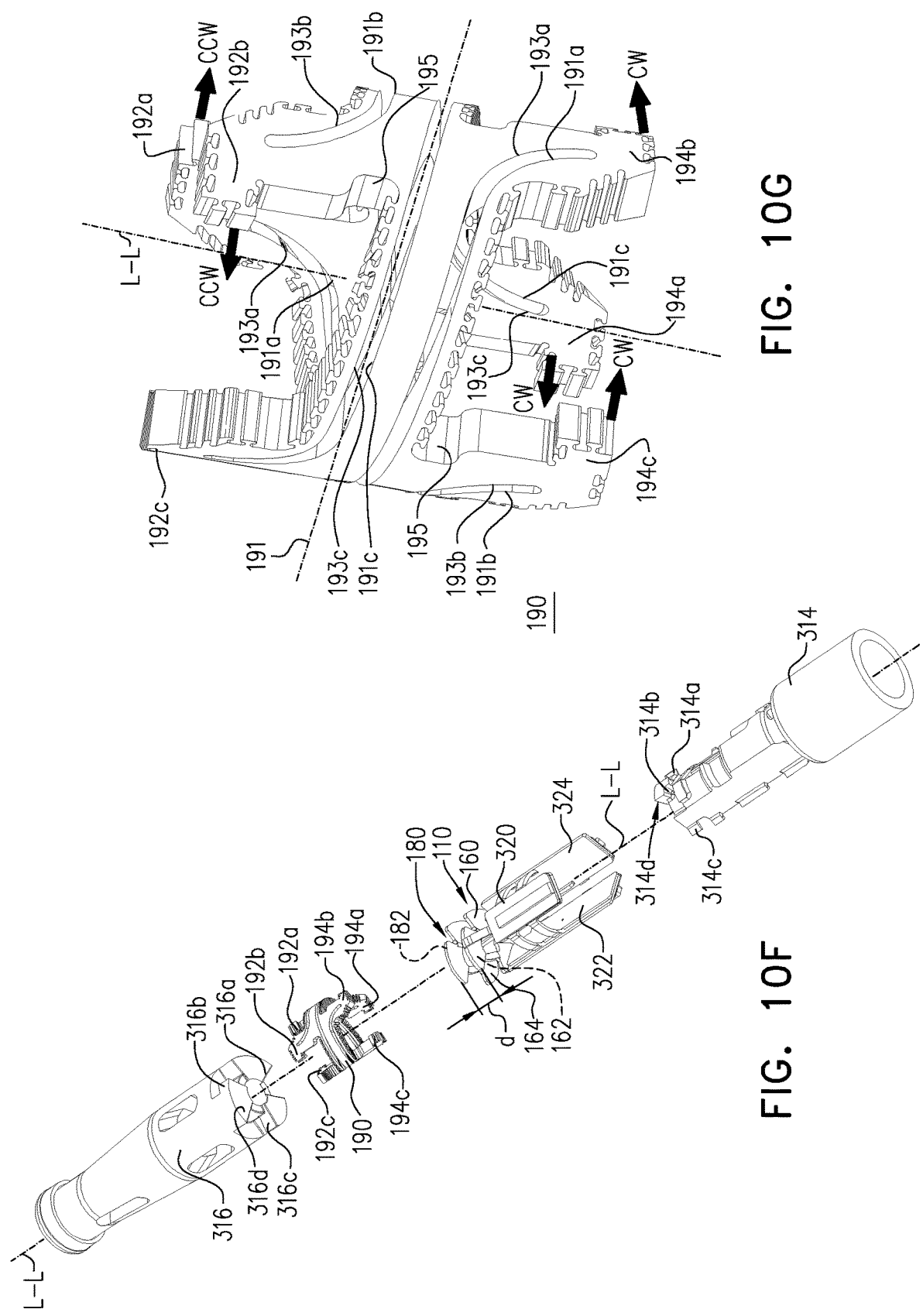

BALLOON CATHETER WITH FORCE SENSOR

RELATED APPLICATION INFORMATION

The present application claims benefit of U.S. Provisional Patent Application Ser. No. 62/899,259 of Govari, et al., filed 12 Sep. 2019, the disclosure of which is hereby incorporated by reference as set forth fully herein.

FIELD OF THE INVENTION

The present invention relates to medical instruments, and in particular, to balloon catheters.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to block or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electromechanical sensor within the catheter shaft generates electrical signals corresponding to the amount of movement of the electrode within a distal portion of the catheter shaft. An output device receives the electrical signals for assessing a level of contact between the electrode and a tissue.

U.S. Patent Application Publication No. 2009/0093806 to Govari et al., which is herein incorporated by reference, describes another application of contact pressure measurement, in which deformation in response to pressure on a resilient member located at the distal end of a catheter is measured using a sensor.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known than impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

U.S. Pat. No. 9,168,004 to Gliner, at al., which is herein incorporated by reference, describes using machine learning to determine catheter electrode contact. The '004 Patent describes cardiac catheterization being carried out by memorizing a designation of a contact state between an electrode of the probe and the heart wall as an in-contact state or an out-of-contact state, and making a series of determinations of an impedance phase angle of an electrical current passing through the electrode and another electrode, identifying maximum and minimum phase angles in the series, and defining a binary classifier adaptively as midway between the extremes. A test value is compared to the classifier as adjusted by a hysteresis factor, and a change in the contact state is reported when the test value exceeds or falls below the adjusted classifier.

US Patent Publication 2015/0141987 of Caplan, et al., describes a device for ablating target tissue of a patient with electrical energy is provided. An elongate shaft includes a proximal portion and a distal portion, and a radially expandable element is attached to the distal portion. An ablation element for delivering electrical energy to target tissue is mounted to the radially expandable element. The device can be constructed and arranged to ablate the duodenal mucosa of a patient while avoiding damage to the duodenal adventitial tissue. Systems and methods of treating target tissue are also provided.

PCT Patent Publication WO 2011/139589 of Medtronic Ardian LLC describes catheter apparatuses, systems, and methods for achieving renal neuromodulation by intravascular access are disclosed herein. One aspect is directed to apparatuses, systems, and methods that incorporate a catheter treatment device comprising an elongated shaft. The elongated shaft is sized and configured to deliver an energy delivery element to a renal artery via an intravascular path. Thermal or electrical renal neuromodulation may be achieved via direct and/or via indirect application of thermal and/or electrical energy to heat or cool, or otherwise electrically modulate, neural fibers that contribute to renal function, or of vascular structures that feed or perfuse the neural fibers.

US Patent Publication 2005/0203597 of Yamazaki, et al., describes a catheter for treating arrhythmia comprises a catheter shaft of a double-cylinder structure where an inner shaft is slidably inserted in an outer shaft, a balloon installed so as to straddle between the tip portion of the inner shaft and the tip portion of the outer shaft, a pair of high frequency current-carrying electrodes of which at least one electrode is provided inside the balloon, and a temperature sensor for monitoring the temperature in the balloon. The front edge portion of the balloon at least in a deflated state protrude from the tip portion of the inner shaft. Alternatively, a tube that is more flexible than the inner shaft is provided on the tip portion of the inner shaft.

U.S. Pat. No. 4,744,366 to Jang describes a catheter for performing balloon angioplasty comprising concentric, independently inflatable/deflatable balloons, each balloon having a different diameter.

US Patent Publication 2018/0280080 of Govari, et al., describes a medical apparatus, including a probe having a distal end configured for insertion into a body cavity and containing a lumen that opens through the distal end, and an inflatable balloon deployable through the lumen into the body cavity such that when the balloon is deployed through the lumen and inflated, a distal pole on a distal side of the balloon is located opposite the lumen. The medical apparatus also includes an electrode attached to the distal side of the inflatable balloon and extending over at least 50% of an area of the distal side of the balloon that is within 30° of arc from the distal pole.

SUMMARY

There is provided in accordance with an embodiment of the present disclosure, a system including a balloon catheter configured to be inserted into a body-part of a living subject, the balloon catheter including an insertion tube having a distal tip, a force sensor connected to the distal tip, and an inflatable balloon including a proximal portion connected to the force sensor so that the force sensor is disposed between the distal tip of the insertion tube and the inflatable balloon, and multiple electrodes disposed around an outer surface of the balloon, and configured, when the balloon is inflated, to contact tissue at respective locations in the body-part, wherein the force sensor is configured to output at least one force signal indicative of a magnitude and a direction of a force applied by the balloon on the tissue when the balloon is inflated.

Further in accordance with an embodiment of the present disclosure, the system includes a display, and processing circuitry configured to compute the magnitude and direction of the force responsively to the at least one force signal, and render to the display a representation of a force vector and a representation of the inflatable balloon, responsively to the at least one force signal.

Still further in accordance with an embodiment of the present disclosure the balloon catheter further includes at least one position sensor configured to output at least one position signal indicative of a position of the distal tip, the processing circuitry is configured to compute the position of the distal tip responsively to the at least one position signal, and render to the display the representation of the force vector responsively to the computed magnitude and direction, and the representation of the inflatable balloon responsively to the computed position and the at least one force signal.

Additionally in accordance with an embodiment of the present disclosure the processing circuitry is configured to receive contact signals from the electrodes, in response to the contact signals, assess a respective quality of contact of each of the electrodes with the tissue, and render to the display the representation of the inflatable balloon, while modifying a visual feature of ones of the electrodes responsively to the respective quality of contact of the electrodes with the tissue at the respective locations.

Moreover, in accordance with an embodiment of the present disclosure each of the electrodes is a flexible electrode formed from a polyamide substrate with a gold covering thereon.

There is provided in accordance with another embodiment of the present disclosure, a electrophysiology catheter device, including a tubular member extending along a longitudinal axis from a proximal portion to a distal portion, a first coupler member connected to the distal portion of the tubular member, a beam coupling member coupled to the first coupler member with at least one first protrusion on one of the beam coupling member and first coupler member with the one first protrusion mated to at least one first notch on one of the other of the beam coupling member and first coupler member, and a second coupler member coupled to the beam coupling member with at least one second protrusion on one of the beam coupling member and second coupler member with the at least one second protrusion mated to at least one second notch on one of the other of the beam coupling member and second coupler member.

Further in accordance with an embodiment of the present disclosure, the device includes a balloon connected to the second coupler member.

Still further in accordance with an embodiment of the present disclosure the beam coupling member defines a generally cylindrical surface that extends from a first end to a second end, each of the first and second ends having at least one arm extending along the longitudinal axis, the at least one arm defining a protrusion that extends along a circumferential direction about the longitudinal axis.

Additionally, in accordance with an embodiment of the present disclosure the at least one arm at the first end includes three arms that extend towards the first coupler member and the at least one arm at the second end includes three arms that extend toward the second coupler member, each arm having a protrusion that extends along a circumferential direction about the longitudinal axis.

Moreover, in accordance with an embodiment of the present disclosure a protrusion proximate the first end is configured to be divided into two ramps that extend in a spiral direction along the longitudinal axis towards another protrusion proximate the second end.

Further in accordance with an embodiment of the present disclosure the first coupler includes a notch configured to mate to the protrusion of the at least one arm at the first end and the second coupler member includes a notch configured to mate to the protrusion of the at least one arm at the second end.

Still further in accordance with an embodiment of the present disclosure, the device includes a flex circuit having at least one location sensing coil mounted to one of the first and second coupler members.

Additionally, in accordance with an embodiment of the present disclosure the at least one location sensing coil includes two location sensing coils.

Moreover, in accordance with an embodiment of the present disclosure, the device includes at least one ablation electrode coupled to the second coupler member and at least one temperature sensor coupled to the second coupler member.

Further in accordance with an embodiment of the present disclosure, the device includes at least one ablation electrode mounted on the balloon and at least one temperature sensor mounted to the balloon.

Still further in accordance with an embodiment of the present disclosure the at least one ablation electrode includes eight ablation electrodes and the at least one temperature sensor includes eight temperature sensors.

BRIEF DESCRIPTION OF THE DRAWINGS

The present invention will be understood from the following detailed description, taken in conjunction with the drawings in which:

FIG. 10F is an exploded view of particular components of FIG. 10E, such that when assembled are lined up with longitudinal axis L-L;

FIG. 10G is a perspective view of the beam coupling member shown in FIG. 10F;

DESCRIPTION OF EXAMPLE EMBODIMENTS

Overview

Figure 1:
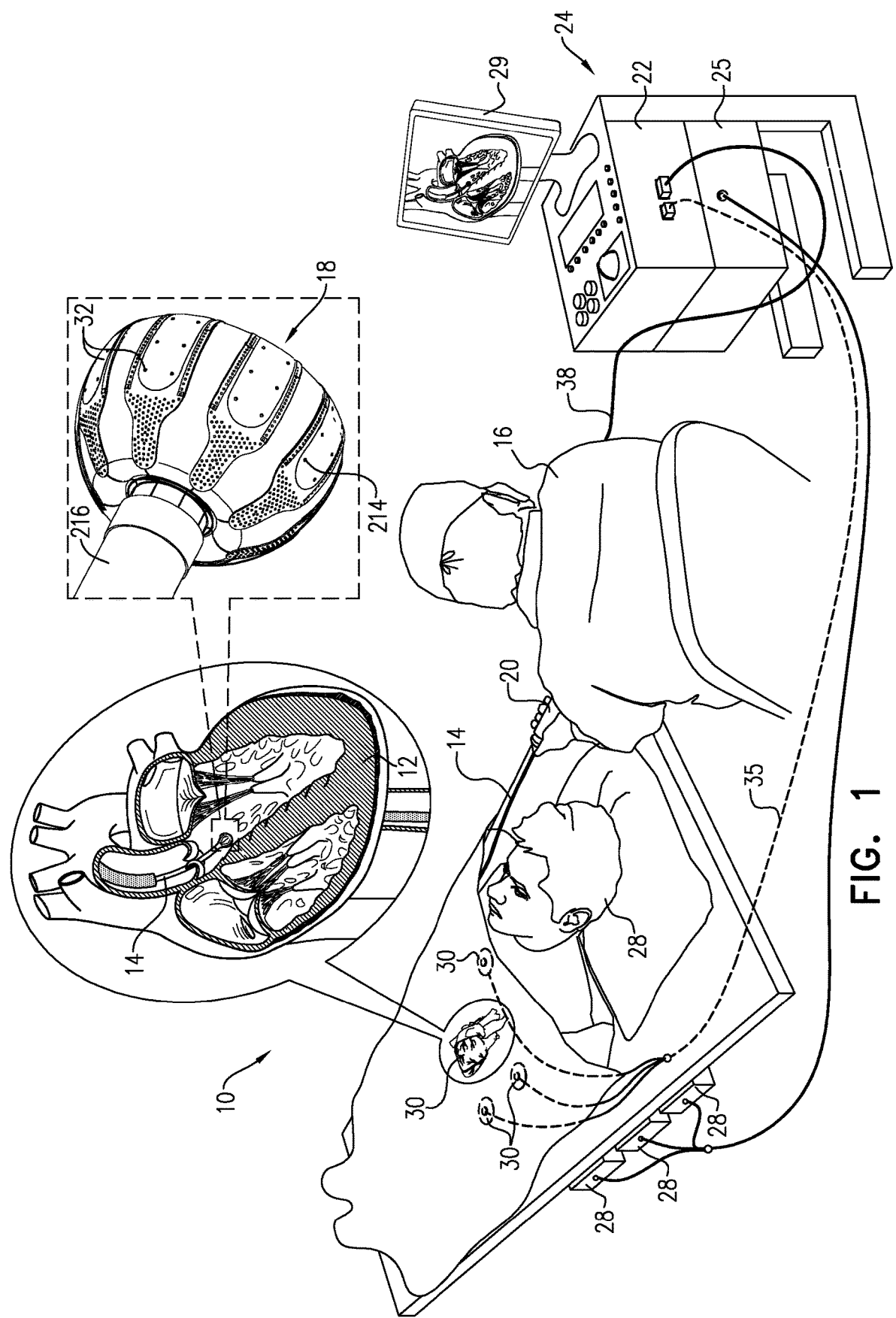
FIG. 1 is a pictorial illustration of a system for evaluating electrical activity in a heart of a living subject and providing treatment thereto using a catheter constructed and operative in accordance with an embodiment of the present invention.

Balloon catheters may inflate to diameters that are approximately 25 mm or more and are generally used to simultaneously perform ablations over a relatively large area, such as a pulmonary vein ostium. Focal catheters, on the other hand, generally having a diameter of around 2.5 mm, are more suited to performing relatively "pin-point" ablations in the heart chamber. To enlarge the ablation region, the focal catheter may be used for multiple consecutive ablations. Performing point-by-point ablation using a focal catheter is time consuming, which may be a critical factor when performing heart procedures.

Embodiments of the present invention overcome the above problems by providing a system including a balloon catheter having a diameter of around 15 mm, or less, when fully inflated. Due to the small size of the balloon, after deflation, the balloon shrinks to a diameter of around 3 mm without the need for a central extension tube, used in many balloon structures, to straighten out the deflated balloon for reinsertion into a sheath.

The inflatable balloon may be maneuvered easily around the chambers of the heart, allowing ablation of large regions of heart tissue to be performed quickly, thus shortening the ablation time compared to a focal catheter.

The inflatable balloon includes flexible electrodes disposed thereon for sensing electrical signals and/or applying radio frequency energy to perform ablation. Wires extending from the rear of the electrodes may also function as temperature sensors for use in sensing the temperature of the electrodes and/or tissue during ablation.

The maneuverability of the inflated balloon within the chambers of the heart highlights a new problem: A large balloon, which performs ablation in a pulmonary vein, occludes the vein due to its large size, and all the electrodes around the surface of the balloon contact the vein tissue sufficiently to provide a good lesion. With a small balloon, however, sufficient electrode contact with the tissue is not guaranteed.

Embodiments of the present invention overcome the above problem by providing the balloon catheter with a force sensor, which is disposed between the distal tip of the deflectable segment of the catheter and the proximal end of the inflatable balloon. The force sensor senses the magnitude and direction of the force applied by the inflatable balloon. In some embodiments, a force vector representing the magnitude and direction of the force may be rendered to a display with a representation of the balloon catheter. The force vector may be used by an operator of the system to estimate the magnitude and direction of the force applied on the heart tissue by the balloon and thereby to configure which electrodes should be used to perform an ablation, with which power, and for which duration. In some embodiments, the force vector may be indicative of the force applied on the balloon by the heart tissue.

In some embodiments of the present invention, sufficiency of tissue contact between individual electrodes and tissue is used to decide whether or not to highlight the electrodes on the representation of the inflatable balloon rendered to the display. The quality of contact may be assessed based on different methods including using impedance values and/or change of phase of impedances, or based on amplitudes of intracardiac electrogram (IEGM) signals, for example only, as will be described below in more detail. Although the quality of contact based on impedance or other electrical methods may provide an indication of whether the electrode is in contact with (or at least close to) the tissue, the impedance does not generally provide an accurate picture as to the extent of the contact. Using the quality of contact in combination with the force vector provides the operator of the system with a more accurate picture of the extent of the contact. The operator of the system may then consider both the force vector and the highlighted electrodes to configure which electrodes should be used to perform an ablation, with which power, and for which duration. For example, the highlighted electrodes may be confirmed by an operator as being in sufficient contact with tissue based on the direction of the force vector. By way of another example, if the force vector indicates that the applied force is low, and the direction of the force is consistent with the highlighted electrodes, and the highlighted electrodes indicate that many of the electrodes are in contact with tissue, the operator may assume that the catheter is in a region of soft tissue as the catheter has likely sunk into the tissue and is partially, or fully, surrounded by the tissue. The operator may then use this information to set the power and duration of ablation according to the assumption that the tissue is soft tissue, by using a lower power for less time. By way of yet another example, if the force vector indicates that the applied force is high, and the direction of the force is consistent with the highlighted electrode(s), and the highlighted electrode(s) indicate that one or two electrodes are in contact with the tissue, the operator may assume that the catheter is in a region of hard tissue (e.g., scarred tissue). The operator may then use this information to set the power and duration of ablation according to the assumption that the tissue is hard tissue, by using a higher power for more time.

In response to signals provided by the catheter electrodes (and optionally body surface electrodes), processing circuitry may assess the respective quality of contact of each of the catheter electrodes with the tissue in the heart. Any one of the catheter electrodes may be in full or partial contact with the tissue of the heart. In some cases, any one of the catheter electrodes may be in contact with the tissue via another fluid such as blood of various thicknesses. The quality of contact (full or partial contact, or contact via another liquid) of any one of the catheter electrodes with the tissue may be assessed based on the signals provided by the catheter.

The term "quality of contact" as used in the specification and claims is defined herein as a quantitative indicator of the degree of electrical contact between one of the catheter electrodes and the tissue. The "quality of contact" may be expressed directly, for example in terms a measured electrical impedance, or indirectly, for example in terms of IEGM amplitude.

In some embodiments, the catheter may provide signals which provide an indication of impedance between the catheter electrodes and body surface electrodes. The indication of the impedance provides an indication of a quality of contact. Since myocardium has a lower conductivity than blood, a higher value of impedance between one catheter electrode and the body surface electrodes indicates a higher quality of contact between that catheter electrode and the tissue. A value of impedance may be selected to define a minimum quality of contact considered to represent sufficient contact between any one of the catheter electrodes and the tissue.

In some embodiments, the impedance between one of the catheter electrodes and another one of the electrodes on the catheter may be used as a measure of quality of contact. As disclosed in the '529 patent mentioned in the background section above, impedance through blood is generally lower than impedance through tissue. Accordingly, tissue contact may be assessed by comparing impedance values across a set of electrodes to premeasured impedance values when an electrode is known to be in sufficient contact with tissue and when it is known to be in contact only with blood.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Reference is now made to FIG. 1, which is a pictorial illustration of a system 10 for evaluating electrical activity in a heart 12 of a living subject and providing treatment thereto using a catheter 14 constructed and operative in accordance with an embodiment of the present invention. The catheter 14 is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference in their entirety. One commercial product embodying elements of system 10 is available as the CARTO® 3 System, available from Biosense Webster, Inc., 31 Technology Drive, Irvine, CA, 92618.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to target tissue. The energy is absorbed in the tissue, heating it to a point (typically above 50° C.) at which point it permanently loses its electrical excitability. This procedure creates non-conducting lesions in the cardiac tissue, which disrupt the abnormal electrical pathway causing the arrhythmia. Such principles can be applied to different heart chambers to diagnose and treat many different types of cardiac arrhythmias.

The catheter 14 typically includes a handle 20, having suitable controls on the handle to enable the operator 16 to steer, position and orient the distal end of the catheter as desired for the ablation. To aid the operator 16, distal portion 18 of catheter 14, or portions proximate thereto, contains position sensors, e.g., traces or coils (discussed below), that provide signals to a processor 22, located in a console 24.

Ablation energy and electrical signals can be conveyed to and from the heart 12 through one or more ablation electrodes 32 located at or near the distal tip 18 via cable 38 to the console 24. Pacing signals and other control signals may be conveyed from the console 24 through the cable 38 and the electrodes 32 to the heart 12.

Wire connections 35 link the console 24 with body surface electrodes 30 and other components of a positioning sub-system for measuring location and orientation coordinates of the catheter 14. The processor 22 or another processor may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference in its entirety. A temperature sensor typically a thermocouple or thermistor, may be mounted on or near each of the electrodes 32. An example of the temperature sensor as used in conjunction with the ablation electrode is shown and described in U.S. patent application Ser. No. 15/939,154 filed on Mar. 28, 2018, which is incorporated by reference with a copy provided in the Appendix in the priority patent application.

The console 24 typically contains one or more ablation power generators 25. The catheter 14 may be adapted to conduct ablative energy to the heart using any known ablation technique, e.g., radiofrequency energy, ultrasound energy, cryogenic energy, and laser-produced light energy. Such methods are disclosed in commonly assigned U.S. Pat. Nos. 6,814,733, 6,997,924, and 7,156,816, which are herein incorporated by reference in their entirety.

The positioning subsystem may also include a magnetic position tracking arrangement that determines the position and orientation of the catheter 14 by generating magnetic fields, using magnetic field generators 28, in a predefined working volume and sensing these fields at the catheter, using coils or traces disposed within the catheter, typically proximate to the tip. A positioning subsystem is described in U.S. Pat. No. 7,756,576, which is hereby incorporated by reference in its entirety, and in the above-noted U.S. Pat. No. 7,536,218.

Operator 16 may observe and regulate the functions of the catheter 14 via console 24. Console 24 includes the processor 22 implementing processing circuitry including appropriate signal processing circuits. The processor 22 is coupled to drive a display 29. The signal processing circuits typically receive, amplify, filter and digitize signals from the catheter 14, including signals generated by sensors such as electrical, temperature and contact force sensors, and a plurality of location sensing coils or traces located distally in the catheter 14. The digitized signals are received and used by the console 24 and the positioning subsystem to compute the position and orientation of the catheter 14, and to analyze the electrical signals from the electrodes and the contact force sensors.

In order to generate electroanatomic maps, the processor 22 typically comprises an electroanatomic map generator, an image registration program, an image or data analysis program and a graphical user interface configured to present graphical information on the display 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. The system 10 typically also includes a reference position sensor, either on an externally applied reference patch attached to the exterior of the subject's body, or on an internally placed catheter, which is inserted into the heart 12 maintained in a fixed position relative to the heart 12. Conventional pumps and lines for circulating liquids through the catheter 14 for cooling the ablation site may be provided. The system 10 may receive image data from an external imaging modality, such as an MRI unit, CT, or the like and includes image processors that can be incorporated in or invoked by the processor 22 for generating and displaying images.

FIGS. 2-8 describe force and position sensors for use in the distal tip of the catheter 14. The sensors generally need to fit within the small inner diameter of the catheter (e.g., often equal to or less than about 2.5 mm) yet overcome various design constraints related thereto to provide feedback reliably. For example, metal coils may be used to detect location within a magnetic field. Generally, larger and thicker coils may provide better detection than smaller and thinner coils, however, due to the small space within the catheter, the coils need to be small and thin enough to fit therein. Further, when such coils are fabricated as traces on a circuit board or flexible circuit via a lithographic process, the process limits the trace pitch. Although the thickness of the traces may be increased using additional layers lithographically, this option may be expensive and the coils may be compromised insofar as the yield decreases non-linearly with the number of layers. These design challenges are compounded by inclusion of additional structures proximate to the location traces, such as force sensors to provide sub-gram force measurements and reducing cross-talk interference that may arise from packing the structures in a tight space, as well as ease of assembly and safe wiring.

Figure 2:
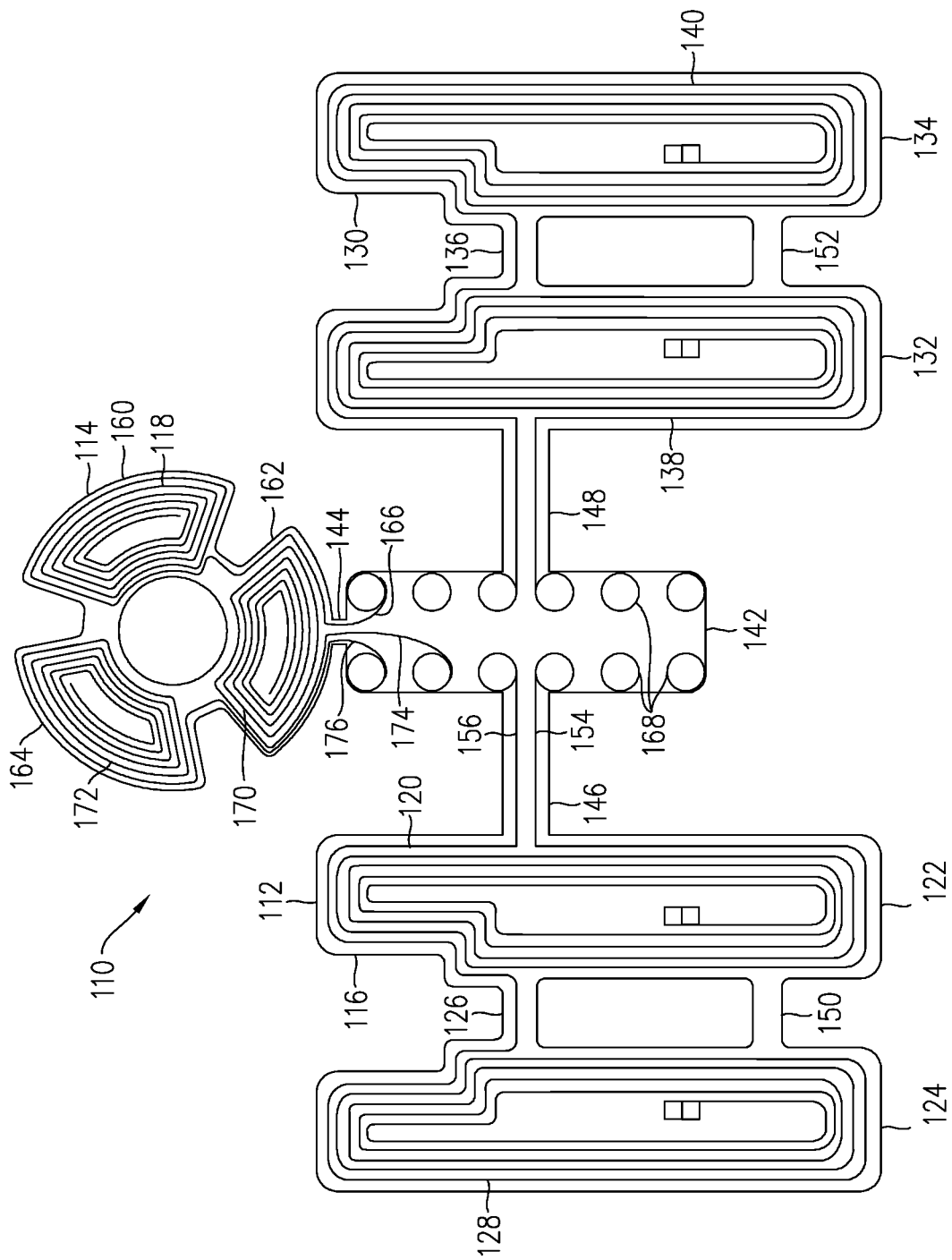
FIG. 2 is a schematic view of a flexible-circuit of the catheter of FIG. 1.

Reference is now made to FIG. 2, which is a schematic view of a flexible-circuit 110 of the catheter 14 of FIG. 1.

The flexible circuit 110 may be employed within a catheter, such as catheter 14, to provide signals indicative of location and force to the processor 22 in console 24. Flexible circuit 110 includes a substantially planar substrate 112 having a first portion 114 having a first shape (e.g., a circular or trefoiled shape as shown) formed from three segments 160, 162, and 164. Flexible circuit 110 also includes a second portion 116 having a second shape (e.g., substantially rectangular as shown) formed from two substantially rectangular segments connected by connector segment 126 and optionally connector segment 150. First portion 114 and second portion 116 are typically different shapes because, as will be explained below, portion 116 is elongated and is assembled with its long axis parallel to the longitudinal axis of the catheter 12, whereas portion 114 is assembled transversely to the longitudinal axis of the catheter 12, such that it should fit in the inner diameter of the catheter 14 (i.e., have a maximum width or diameter that is less than the inner diameter of the catheter 14). Substrate may be formed of any suitable material that is non-conductive and is capable of resisting high temperatures, for example, but not limited to, polyimide, polyamide, or liquid crystal polymer (LCP).

Substrate 112 may also include additional portions, such as third portion 130 and fourth portion 142. Each of these portions may further include various segments. Third portion 130 may have a similar structure to second portion 116, and may include substantially rectangular segments 132, 134, which are connected via at least one connector segment, such as 136 and/or 152. Fourth portion 142 may include at least three connector segments 144, 146 and 148, which connect fourth portion 142 to first, second, and third portions 114, 116, and 130, respectively.

Electrical components may be incorporated into substrate 112 and its various portions and segments. For example, substantially planar coils or traces used to measure signals relating to force (i.e., force-sensing coils or traces) may be disposed on first portion 114. Specifically, a coil 118 may be disposed on segment 160, a coil 170 may be disposed on segment 162, and a coil 172 may be disposed on segment 164. Coils 118, 170, and 172 may be discrete from each other, as shown, or they may each be connected to one or both of the others. Portions of each coil, or extensions thereof, may extend from the coil to solder joints 168 (only some labeled for the sake of simplicity) located on fourth portion 142 and be soldered thereto. Where the three coils are discrete from each other, each should include at least one respective line (e.g., 166, 174, and 176) connecting to the solder joints 168. Where the coils are discrete from each other, the signals generated in each of the coils may be used to provide additional details of force, such as an indication of an off-center force or an off-axis direction of the force. As shown, each coil on first portion 114 includes approximately five turns. However, because signal strength is a function of the number of turns, the number of turns may be maximized based on the size of each segment and the pitch that the lithographic process can accomplish.

Planar coils or traces used to measure signals relating to location (i.e., location coils or traces) may also be incorporated into second portion 116 and third portion 130. Coil 120 may be disposed on segment 122, coil 128 may be disposed on segment 124, coil 138 may be disposed on segment 132, and coil 140 may be disposed on segment 134. Each of the coils 120, 128, 138, 140 may extend to solder joints 168 on fourth portion 142. For example, coil 120 may include an extension 154 that connects to a solder joint 168 via connector segment 146 and coil 128 may include an extension 156 that connects to a solder joint 168 via connector segment 126, segment 122 and connector segment 146. As shown, each coil on portions 116 and 130 includes approximately five turns. However, because signal strength is a function of the number of turns, the number of turns may be maximized based on the size of segments 122, 124, 132, and 134, and the pitch that the lithographic process can accomplish.

Second portion 116 is laterally disposed to one side of first portion 114 and fourth portion 142, and such that third portion 130 is laterally disposed to the other side of first portion 114 and fourth portion 142. Thus, fourth portion 142 is disposed between first portion 114, second portion 116 and third portion 130. Further, segments 122 and 124 have traces wound in opposite orientations.

Substrate 112 may be a single layer. Alternatively, it may include more layers, for example, but not limited to, between two and ten layers, such as, four layers. In this manner the coils may be thickened by adding layers. However, as described above, thickening by layers results in non-linearly decreased yield in manufacturing of the component. The flexibility of flexible circuit 110 provides a solution to this tradeoff, as will be described below.

Figure 3:
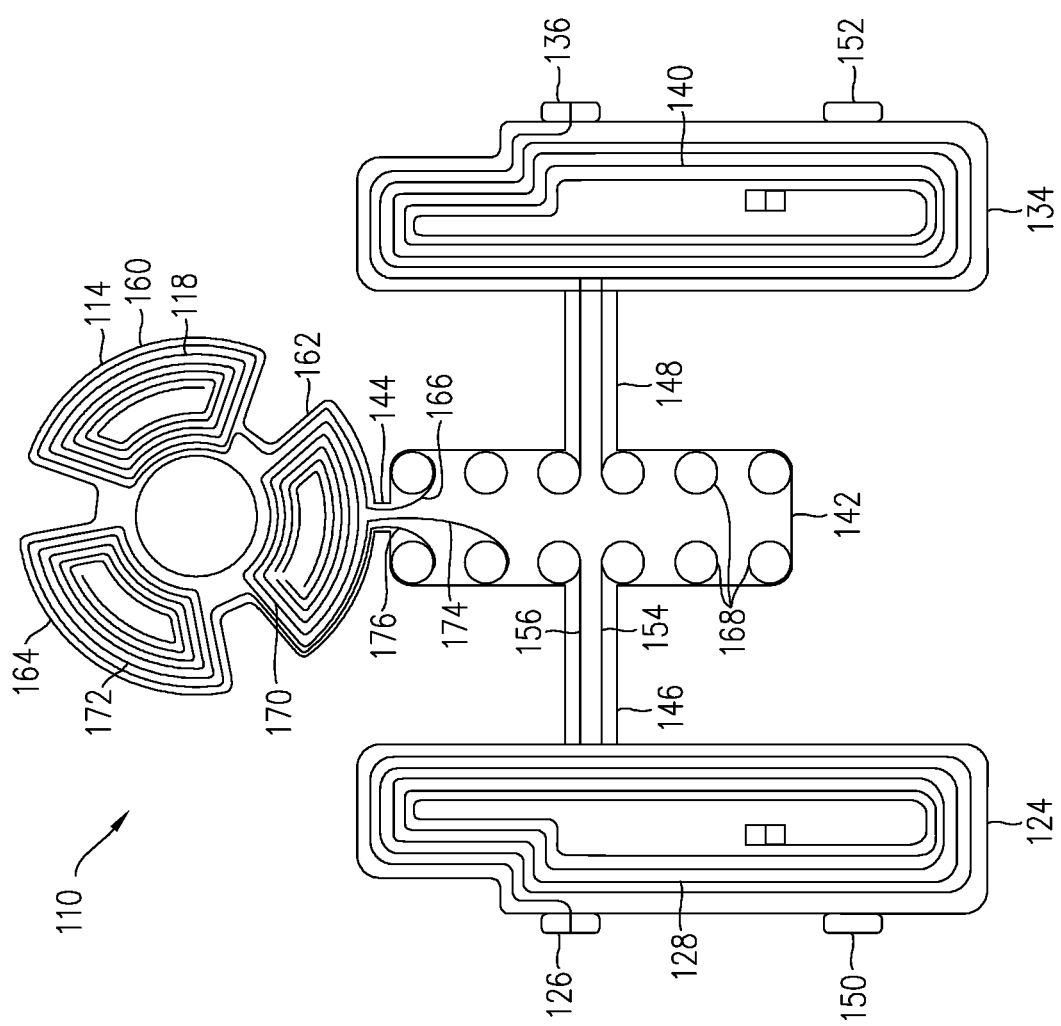
FIG. 3 is a schematic view of the flexible-circuit of FIG. 2 in a folded configuration.

Reference is now made to FIG. 3, which is a schematic view of the flexible-circuit 110 of FIG. 2 in a folded configuration. By deforming or bending connector 126 and connector 150, segment 124 may be folded on top of segment 122 so that coil 128 aligns with coil 120. Similarly, by deforming or bending connector 136 and connector 152, segment 134 may be folded on top of segment 132 so that coil 140 aligns with coil 138. Although connectors 150 and 152 are optional, they may assist aligning the coils with each other by reducing relative rotation between the segments. If substrate 112 is formed from multiple layers, such as four layers, for example, then after segment 124 is folded onto segment 122, coils 120 and 128 form a combined coil having more than two layers, such as eight layers. Folding different segments on to each other to yield a combined coil allows for the creation of a coil with more layers without negatively affecting manufacturing yields.

An advantage that a thinner substrate (e.g., four layers) has over a thicker substrate (e.g., eight layers) is that it is easier to deform or bend, which is helpful for assembling flexible circuit 110 to other catheter components and ultimately for fitting it within the inner-diameter of the catheter, as will be described.

Figure 4:
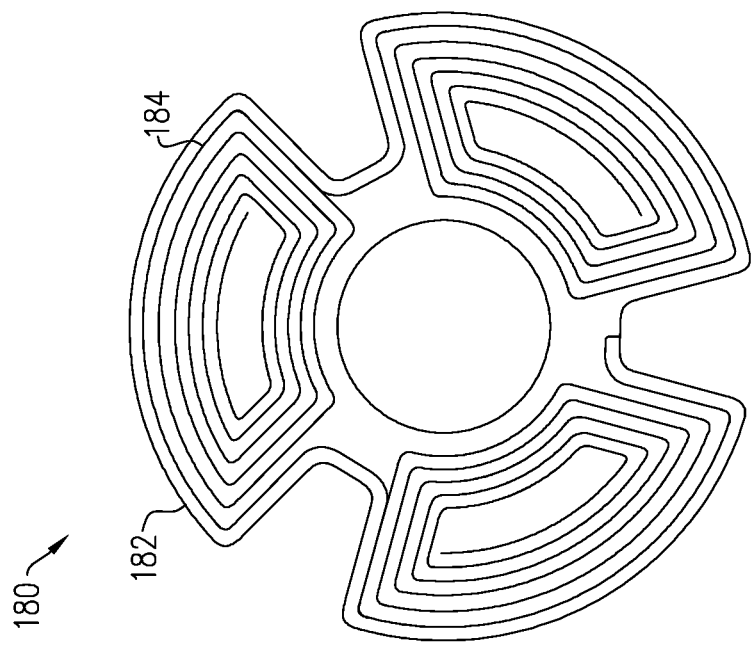
FIG. 4 is a schematic view of another flexible-circuit of the catheter of FIG. 1.

Reference is now made to FIG. 4, which is a schematic view of another flexible-circuit 180 of the catheter 14 of FIG. 1. The flexible circuit 180 includes substrate 182 and coil or coils 184. The structure of flexible circuit 180 is similar to the structure of first portion 114 of flexible circuit 110. However, in various embodiments, the number or pitch of the coils may vary, and the various coils on the three segments may be discrete from each other or integrated with each other.

Figure 5:
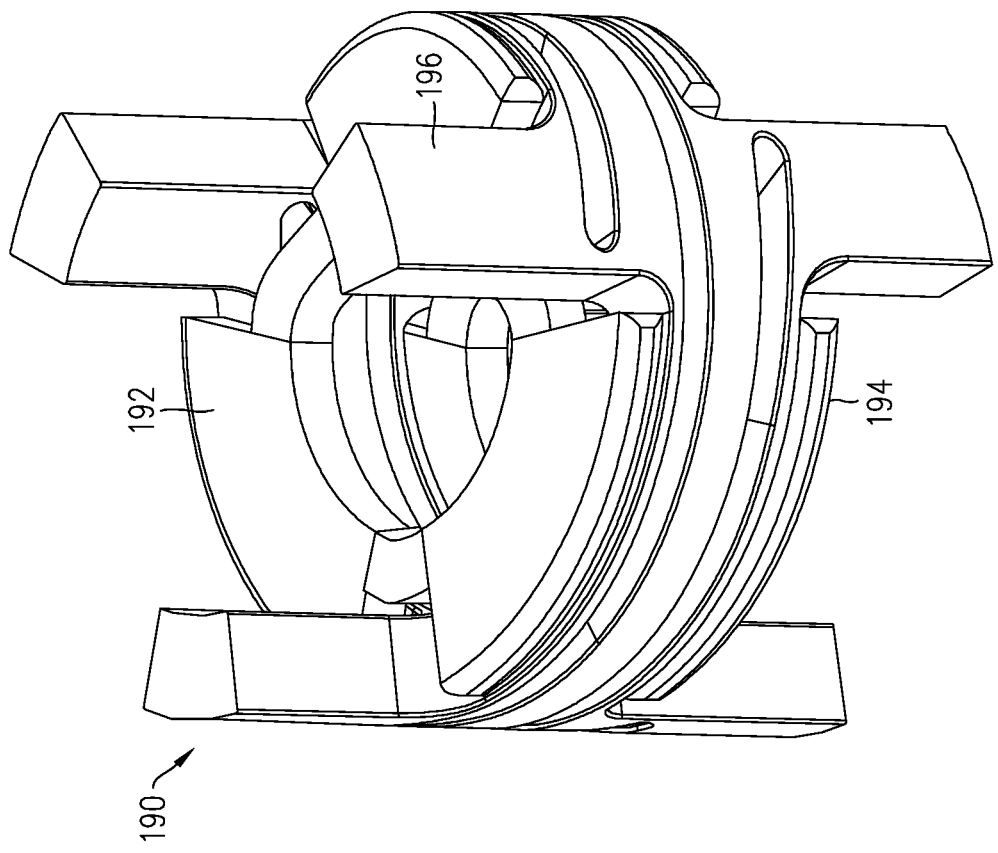
FIG. 5 is a schematic view of a beam coupling member 190 of the catheter of FIG. 1.

Reference is now made to FIG. 5, which is a schematic view of a beam coupling member 190 of the catheter 14 of FIG. 1. The helical beam coupling member 190 includes a top face 192, a bottom face 194, and various arms 196 that may be used to connect the beam coupling member 190 to other components of catheter 14. Beam coupling member 190 has a known or predetermined spring constant providing a relationship between distance and force in accordance with Hooke's law. Together flexible circuit 180, first portion 114 of flexible circuit 110, and helical beam coupling member 190 form a force sensor sub-assembly that receives electrical signals from, and provides electrical signals to, console 24, which may process received signals to determine forces, e.g., sub-gram forces, exerted on tip 18 of catheter 14.

The first portion 114 (including coils 118, 170, 172) of flexible circuit 110 is disposed on bottom face 194, and coils 184 on flexible circuit 180 are disposed on the top face 192. In some embodiments, the first portion 114 (including coils 118, 170, 172) of flexible circuit 110 is disposed on top face 192, and coils 184 on flexible circuit 180 are disposed on the bottom face 194.

Wires (within a cable-bundle 198 of FIGS. 6 and 7), running between the console 24 and solder joints 168 of fourth portion 142 of flexible circuit 110, connect the console 24 via coil extensions 166, 174, and 176 to coils 118, 170, and 172 on segments 160, 162, and 164 of first portion 114, respectively. Wires (also within cable-bundle 198) running from the console 24 connect with coil or coils 184 on flexible circuit 180. Electrical signals from console 24, e.g., having RF frequencies, may be used to power either the coils 118, 170, 172 on the first portion 114 of flexible circuit 110 or the coils 184 on flexible circuit 180. Whichever set of coils receives power from console 24 may be considered a transmitter (i.e., one of flex circuit 110 or 180) because it emits an electromagnetic field that varies in accordance with the frequency of the signals received from console 24. The set of coils that is not powered by console 24 may be considered a receiver in as much as it functions like an antenna in response to the electromagnetic field from the transmitter. Thus, the receiver (i.e., the other of flex circuit 110 or 180) generates electrical signals that may be conveyed to console 24 for analysis. The electrical signals generated by the receiver depend on the distance between the receiver and the transmitter, such that the electrical signals generated by the receiver may be correlated to the distance between the receiver and the transmitter, which is correlated to a compression displacement of the beam coupling member (e.g., in the order of 100 nanometers) and thus correlates to forces against tip 18 of catheter 14 that cause spring 190 to compress.

The beam coupling member 190 may be deflected to one side more than another. This off-center deflection is representative of a sideways component of a force being applied by the tip 18. The sideways force may be detected by the different distances between the coils 118, 170, 172 and the coil(s) 184 which may be computed for example, from the signals provided by the coils 118, 170, 172.

In use, console 24 may process these signals and use them to regulate the amount of ablation energy supplied to electrodes. For example, when the signals indicate that the beam coupling member 190 is in a relaxed state (i.e., no compression) this may be perceived as an indication that tip 18 of catheter 14 is not in contact with tissue, and therefore, no ablation energy should be supplied to the electrodes. Indicators of the information (e.g., in units of force, such as gram-force) may further be provided to operator 16 on display 29 so that the operator 16 may adjust the ablation settings manually.

Top distal face 192 and bottom proximal face 194 of beam coupling member 190 may be parallel to each other and oriented transversely to the longitudinal axis of the beam coupling member 190 (e.g., at an angle of greater than about sixty degrees and less than or equal to ninety degrees, e.g., about eighty degrees). Accordingly, in some embodiments, the receiver and the transmitter, affixed thereto, are similarly oriented. The inventors have determined that a transverse but non-perpendicular orientation of the receiver and transceiver increases the sensitivity of the receiver because the distance between the transmitter and receiver is minimized as compared to when the receiver and transceiver are disposed perpendicular to the beam coupling member 190's longitudinal axis, and the catheter's longitudinal axis.

Figure 6:
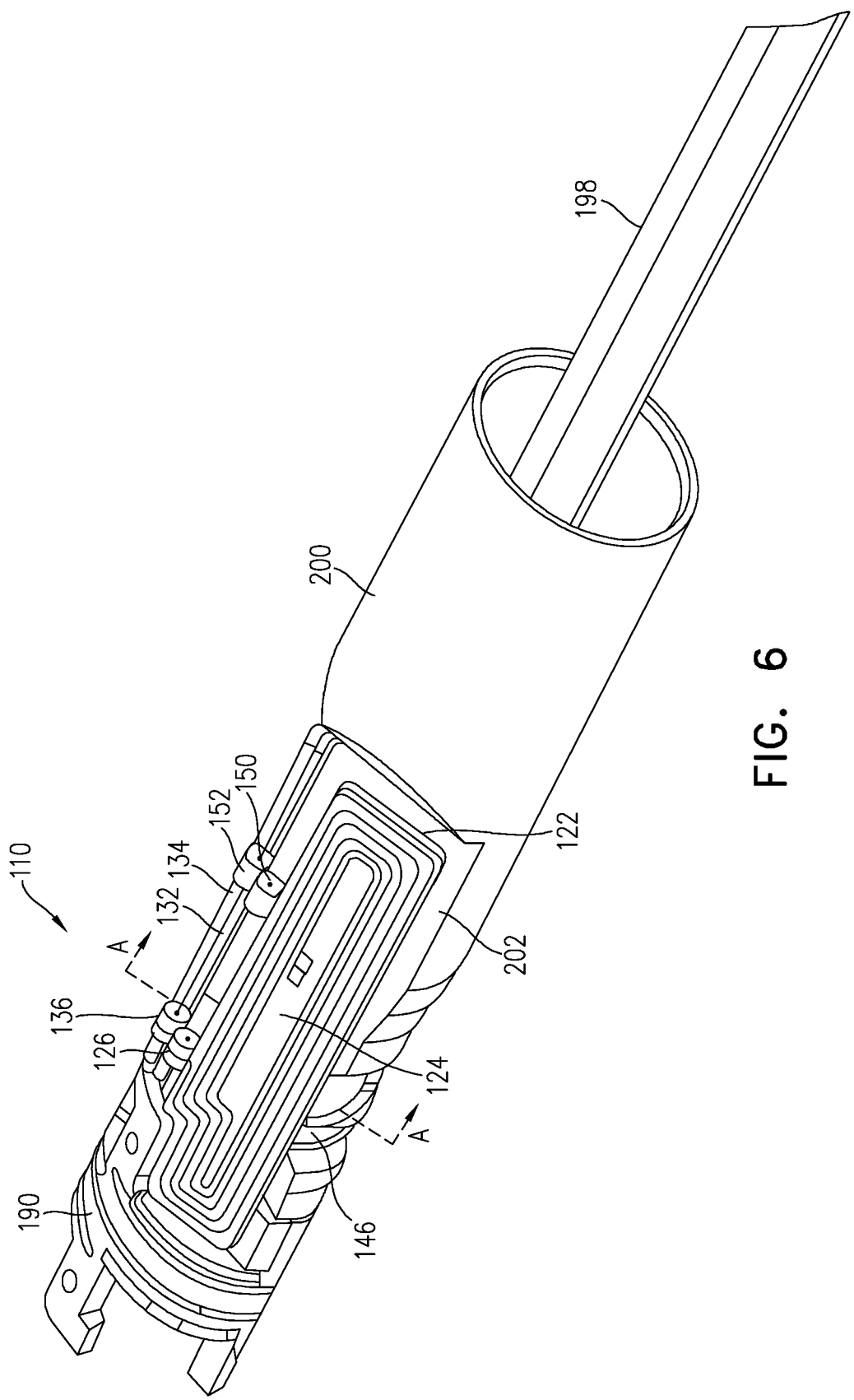
FIG. 6 is a first cutaway view of a distal portion of the catheter of FIG. 1.
Figure 7:
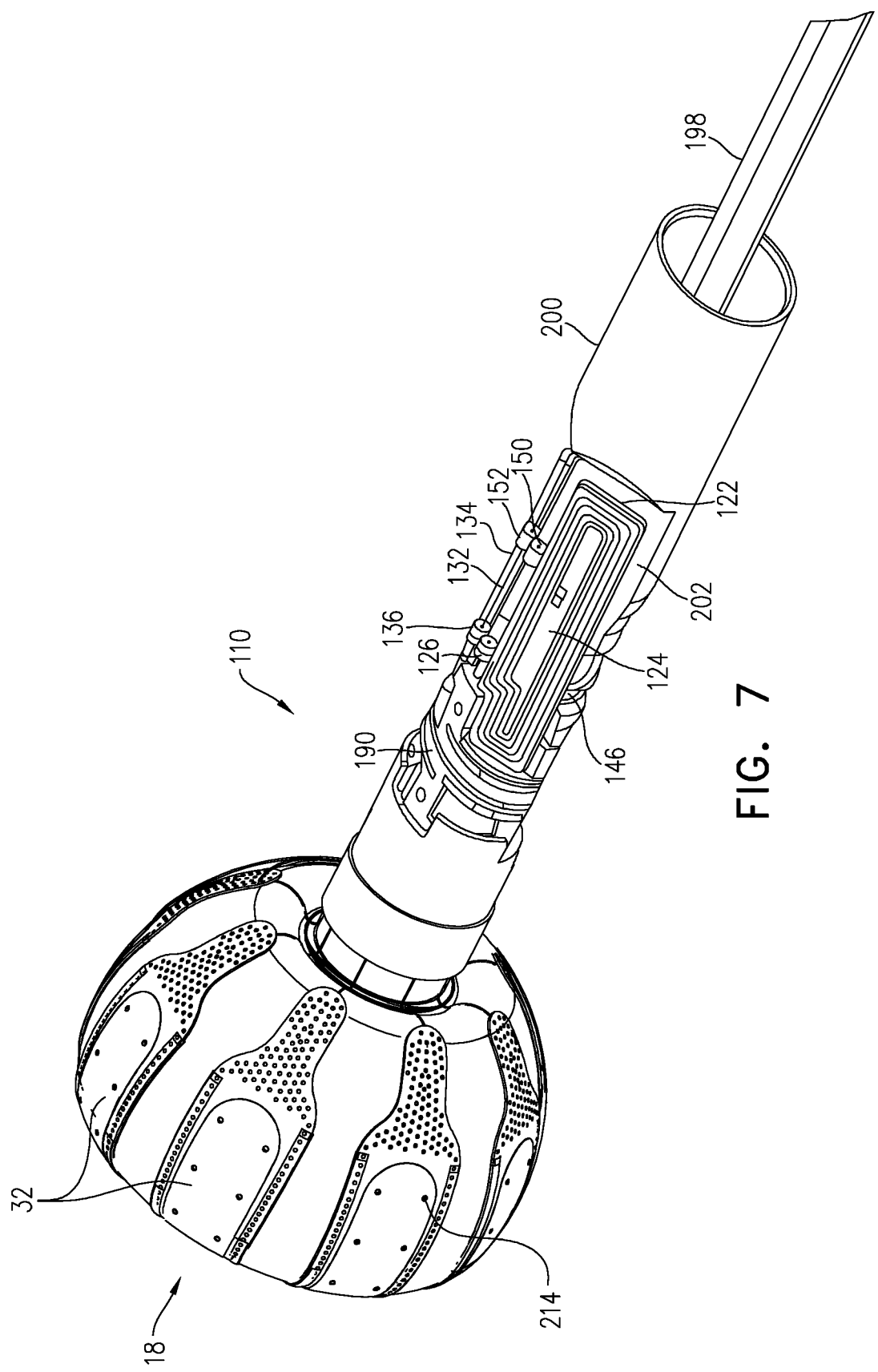
FIG. 7 is a second cutaway view of a distal portion of the catheter of FIG. 1.
Figure 8:
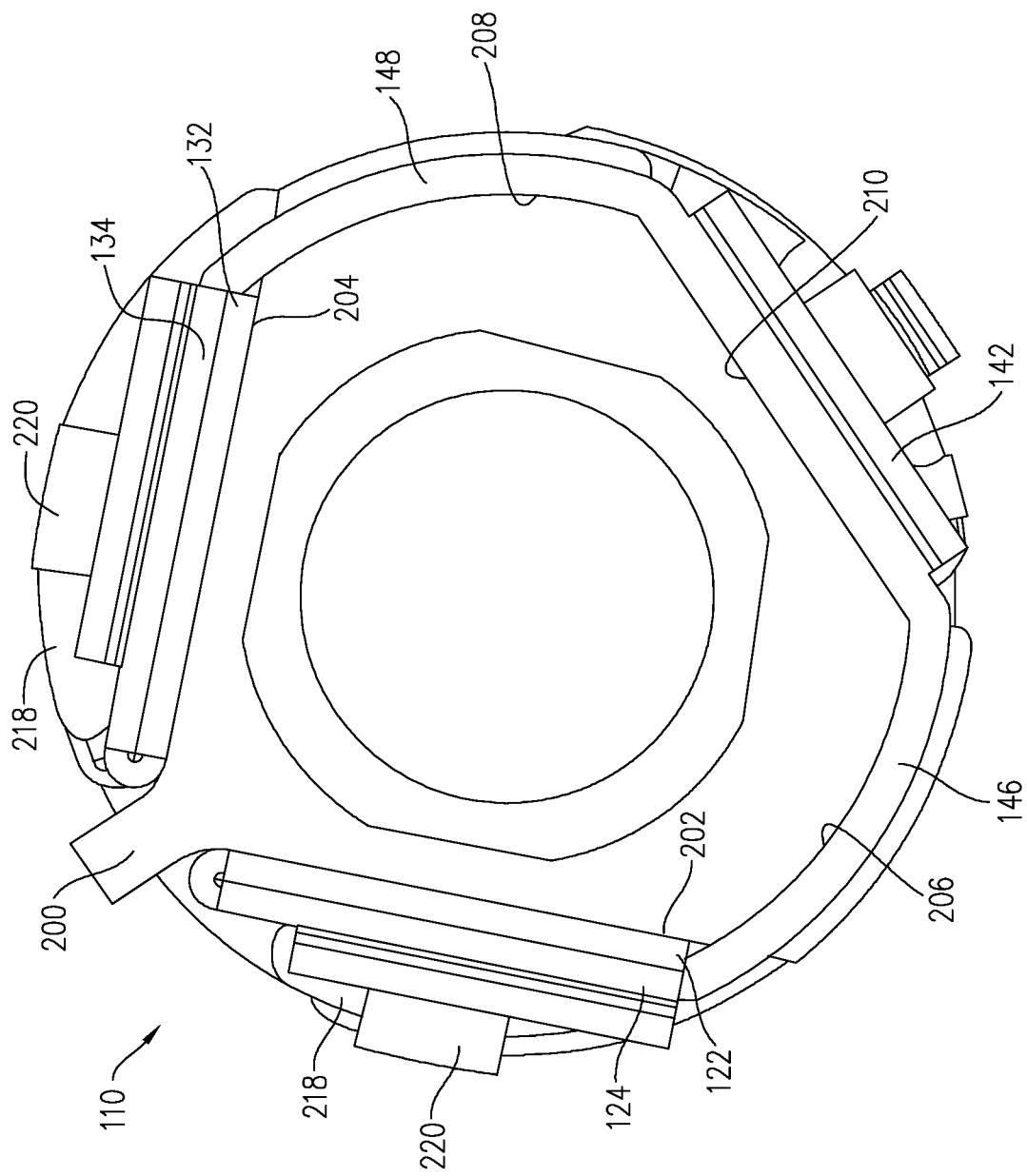
FIG. 8 is a transverse cross-sectional view taken through line A-A of FIG. 6.

Reference is now made to FIGS. 6-8. FIG. 6 is a first cutaway view of a distal portion of the catheter 14 of FIG. 1. FIG. 7 is a second cutaway view of a distal portion of the catheter 14 of FIG. 1. FIG. 8 is a transverse cross-sectional view taken through line A-A of FIG. 6. FIG. 6 shows flexible circuit 110 as assembled to beam coupling member 190 and a coupler or coupling sleeve 200. Although not seen, first portion 114 of flexible circuit 110 is adhered to proximal face 194 (FIG. 5) of beam coupling member 190 and flexible circuit 180 is adhered to distal face 192 (FIG. 5) of beam coupling member 190. In FIG. 7, tip 18, which includes ablation electrode(s) 32, and various irrigation apertures 214, is attached to beam coupling member 190. Also shown in FIGS. 6 and 7 is cable bundle 198. Cable bundle 198 includes a set of wires which, although not shown, are connected to solder joints 168 on fourth portion 142 of flexible circuit 110, and thus to the various coils or traces on flexible circuit 110, and to coils or traces 184 on flexible circuit 180. As seen in FIG. 6-8 flexible circuit 110 is no longer planar. Rather, it has been deformed to have a shape that has a traverse cross section that is generally circular. Segment 124 of second portion 116 is the most readily visible segment of flexible circuit 110 in FIGS. 6 and 7. Various sides of segment 122, segment 132, and segment 134, as well as connectors 126, 136, 146, 150, and 152 are also visible in these figures. As seen these connectors have been deformed into bent or curved configurations for attachment to coupler 200. Specifically, segment 122 is adhered to a substantially planar surface 202 of coupler 200, and segment 132 is adhered to a substantially planar surface 204 of coupler 200 (FIG. 8). So assembled, these portions of flexible circuit 110 may be viewed as having a triangular cross section. Further, connector 146 is adhered to a circular (or arcuate) surface 206 of coupler 200 and connector 148 is adhered to a circular (or arcuate) surface 208 of coupler 200. So assembled, these portions of flexible circuit 110 may be viewed as having a circular (or arcuate) cross section. Fourth portion 142 may further be adhered to substantially planar surface 210 of coupler 200.

The diameter or width of the circular portion of the cross section of flexible circuit 110 as assembled to coupler 200 is equal or approximately equal to the diameter or maximum width of first portion 114, which is also equal or approximately equal to the maximum width (or base) of the triangular portion of the cross-section of flexible circuit 110 as assembled to sleeve 100. Accordingly, as assembled, flexible circuit 110, may be readily inserted into an outer tube or sleeve 216 (FIG. 1) that provides an outer surface of catheter 14 and that defines the inner diameter within which components (e.g., flexible circuit 110, beam coupling member 190, coupler 200) of catheter 14 fit. To help prevent soft spots under sleeve 216 that result from gaps between the substantially planar outer surfaces of segments 124 and 134, and portion 142 on the one hand, and the curvature of sleeve 216 on the other hand, these gaps may be filled by including additional material, e.g., adhesives 218 and polyimide layers 220, on segments 124 and 134 (of second portion 116 (FIG. 2) and third portion 130 (FIG. 2), respectively) and portion 142. The polyimide layers 220 may be fabricated separately from flexible circuit 110 and adhered thereto, or they may be an integral portion of flexible circuit 110, formed during the same lithographic process as the remainder of flexible circuit 110. Polyimide layers 220 may interpolate the curve of sleeve 216 with a series of substantially planar steps or layers.

Flexible circuit 110 may be assembled into catheter 14 as follows. First, flexible circuit 110 may be provided. Segment 124 of second portion 116 may be folded over segment 122 of second portion 116 to overlap it and contact it by deforming connector 126 and, if included, connector 150. Segment 134 of third portion 130 may be folded over segment 132 of third portion 130 to overlap it and contact it by deforming connector 136 and, if included, connector 152. First portion 114 of flexible circuit 110 may be oriented to be parallel to bottom face 194 of beam coupling member 190, which is oriented transversely (e.g., less than thirty degrees from a perpendicular plane) to a longitudinal axis of beam coupling member 190. First portion 114 may then be adhered to bottom face 194 of beam coupling member 190. Coupler 200 having substantially planar surface portions may be provided and oriented to align its longitudinal axis with the longitudinal axis of the beam coupling member 190. Second portion 116 and third portion 130 may be oriented to be parallel to respective substantially planar surface portions of coupler 200. Then, second portion 116 and third portion 130 may be adhered to the respective substantially planar surface portions of coupler 200. Coupler 200, adhered to flexible circuit 110, may then be coupled or inserted into outer sleeve 216. Finally, tip 18 may be affixed to beam coupling member 190. Flexible circuit 180 may be adhered to top face 192 of beam coupling member 190 at nearly any step of the process so long as tip 18 has not been attached to beam coupling member 190.

Figure 9:
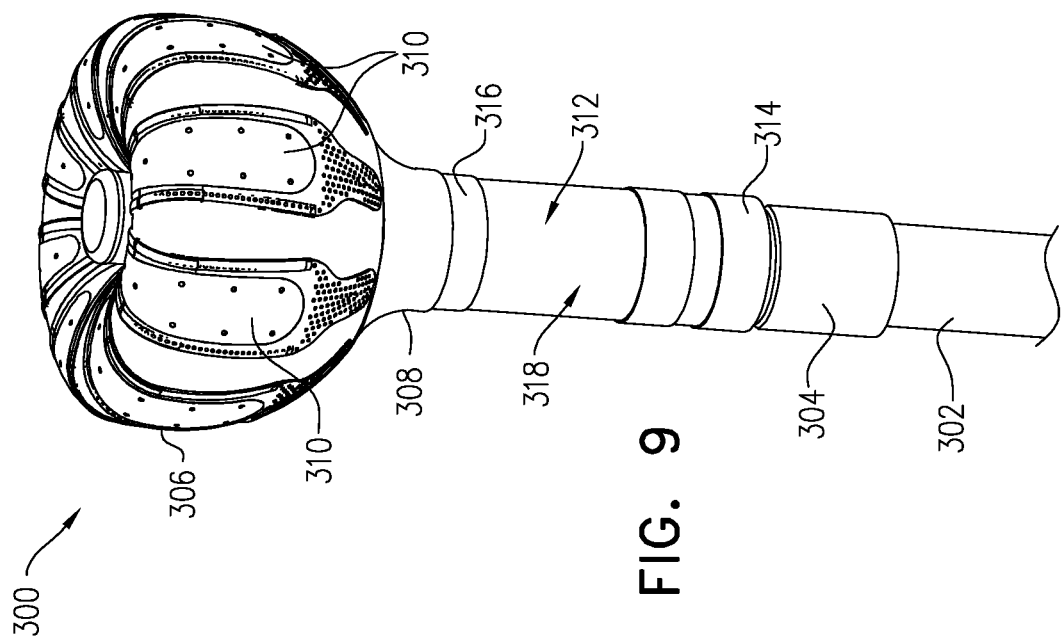
FIG. 9 is a schematic view of a balloon catheter constructed and operative in accordance with an embodiment of the present invention.

Reference is now made to FIG. 9, which is a schematic view of a balloon catheter 300 constructed and operative in accordance with an embodiment of the present invention. Reference is also made to FIGS. 10A-D, which are semi-transparent views of the balloon catheter 300 of FIG. 9. In all subsequent figures herein, it should be understood that beam member 190 of FIG. 5 could be utilized with a particular variation shown and described in FIGS. 10F and 10G.

The balloon catheter 300 is configured to be inserted into a body-part (such as a heart chamber, or any other suitable body-part) of a living subject. The balloon catheter 300 includes an insertion tube 302 having a distal tip 304. The insertion tube 302 may have any suitable outer diameter according to the body-part in which the balloon catheter 300 is to be inserted. In some embodiments, the outer diameter of the insertion tube 302 is about 3 mm.

The balloon catheter 300 includes an inflatable balloon 306 including: a proximal portion 308 connected to the distal tip 304 of the insertion tube 302 via a force sensor 312; and multiple electrodes 310 disposed thereon. The inflatable balloon 306 also includes various irrigation apertures 311 (only one is labeled for the sake of simplicity). The inflatable balloon 306 may have any suitable diameter when fully inflated. In some embodiments, the inflatable balloon 306 has an outer diameter of less than 15 mm. The electrodes 310 are configured to contact tissue at respective locations in the body-part. Each electrode 310 is a flexible electrode formed, for example, from a polyamide substrate with a gold covering thereon, or any other suitable combination of materials. Each electrode 310 is connected to a proximal end of the insertion tube 302 via wires (not shown) which may also function as a temperature sensor to provide a signal indicative of temperature of the electrode 310 for use during ablation.

The balloon catheter 300 includes a force sensor 312 disposed proximate the distal tip 304 of the insertion tube 302 and configured to output at least one force signal indicative of a magnitude and a direction of a force applied by the inflatable balloon 306 when inflated on the tissue. The force sensor 312 is disposed between the distal tip 304 of the insertion tube 302 and the proximal portion 308 of the inflatable balloon 306.

The force sensor 312 is connected to the insertion tube 302 and the inflatable balloon 306 using a lower coupler 314 and an upper coupler 316, respectively. The lower coupler 314 and the upper coupler 316 may use any suitable coupling mechanism, for example, but not limited, a screw fitting, a bayonet fitting, or a pressure fit coupling.

The balloon catheter 300 includes at least one position sensor 318 configured to output at least one position signal indicative of a position of the inflatable balloon 306 and/or the distal tip 304. The position sensor 318 is described in more detail with reference to FIG. 12 and may comprise one or more magnetic coils. In some embodiments, the electrodes 310 may be used as position sensors in conjunction with the body-surface electrodes 30 (FIG. 1) using a current-based, or impedance-based location tracking method, or a combined magnetic and current/impedance-based location tracking method described above in more detail with reference to FIG. 1.

Due to the small size of the balloon, after deflation, the balloon shrinks to a diameter of around 3 mm without the need of a central extension tube, used in many balloon structures, to straighten out the deflated balloon for reinsertion into a sheath. The inflatable balloon may be easily maneuvered around the chambers of the heart, allowing ablation of large regions of heart tissue to be performed quickly, thus shortening the ablation time compared to a focal catheter.

During ablation, RF power may be applied to all the electrodes 310 equally or a multichannel RF generator may be used to selectively apply power to each of the electrodes 310. The power levels may be controlled according to temperature feedback or by manually controlling the power. The electrodes 310 may also be used to sense electrical activity in the body part, for example IEGMs.

Figure 10A:
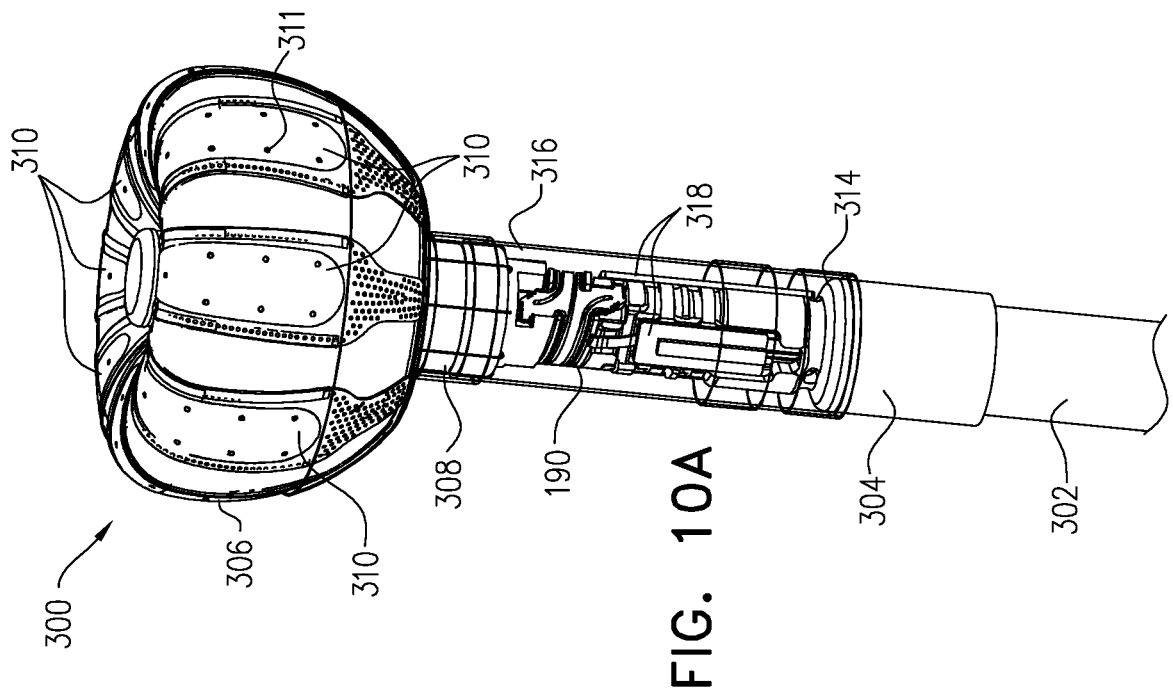
FIG. 10A-D are semi-transparent views of the balloon catheter of FIG. 9.
Figure 10B:
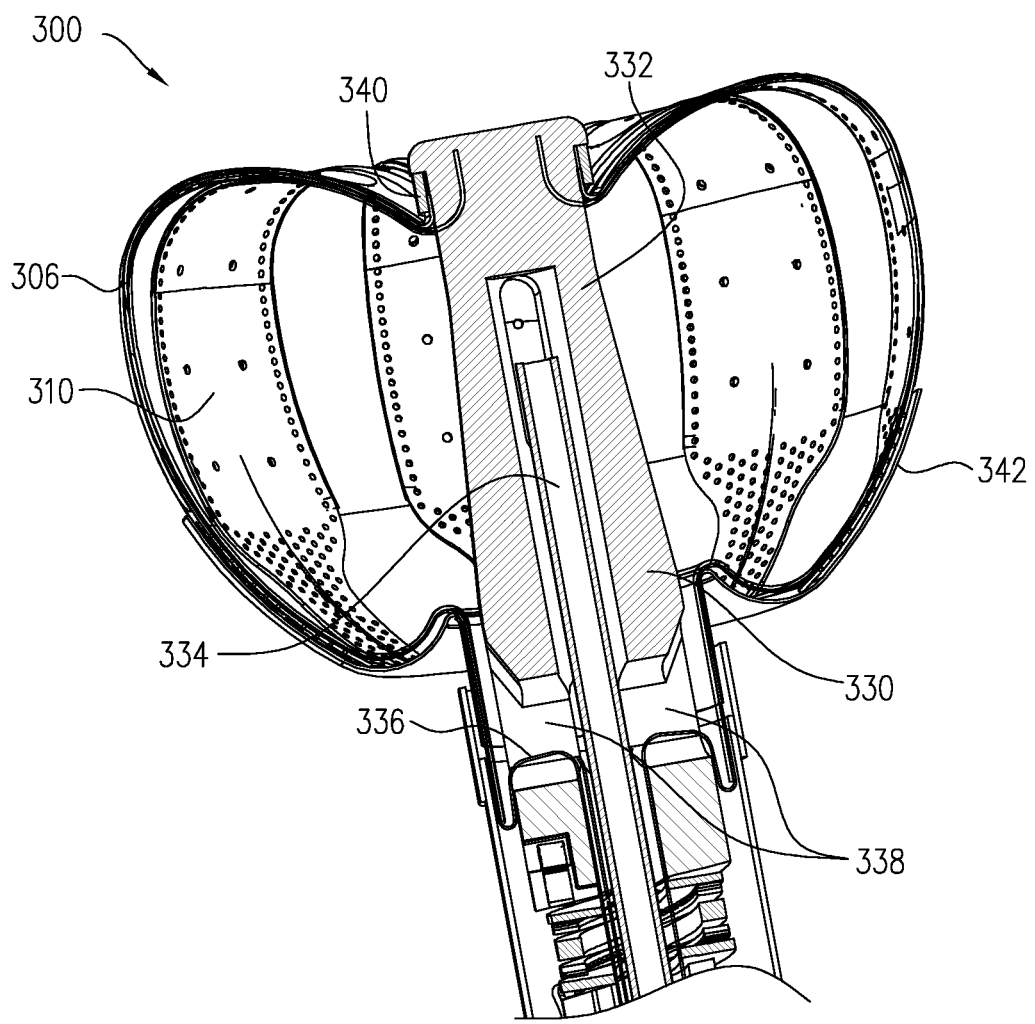

FIGS. 10B and D show a coupler/flow diverter 330 connected to the distal portion of the force sensor 312. The coupler/flow diverter 330 is an elongated element which extends distally and is coaxial with the insertion tube 302 (FIGS. 10A and 10B). An irrigation line 334 is disposed in the insertion tube 302 and extends into a central portion of the coupler/flow diverter 330 and is bonded to a proximal section of the coupler/flow diverter 330. The coupler/flow diverter 330 includes irrigation ports 332 therein through which irrigation fluid enters the inflatable balloon 306 from an opening at the end of the irrigation line 334. Wires 336 (also functioning as temperature sensors) connecting to the electrodes 310 are fed through the insertion tube 302 and exist out of proximal elongated openings 338 in the coupler/flow diverter 330. These openings are then sealed to prevent irrigation fluid from entering the insertion tube 302.

The inflatable balloon 306 is bonded to the proximal section and the distal section of the coupler/flow diverter 330. At the distal section of the inflatable balloon 306, a polymer ring 340 secures the inflatable balloon 306 and/or distal portions of the electrodes 310 to the coupler/flow diverter 330 in order to prevent the electrodes 310 from delaminating. A partial balloon 342 covers the inflatable balloon 306 and the proximal section of the inflatable balloon 306 to protect the wires 336 and non-ablation surfaces of electrodes 310. The partial balloon 342 may be configured to take on a portion of a hemisphere to ensure that certain components such as wirings and circuit trace are protected between the main balloon 306 and the partial balloon 342.

Figure 10C:
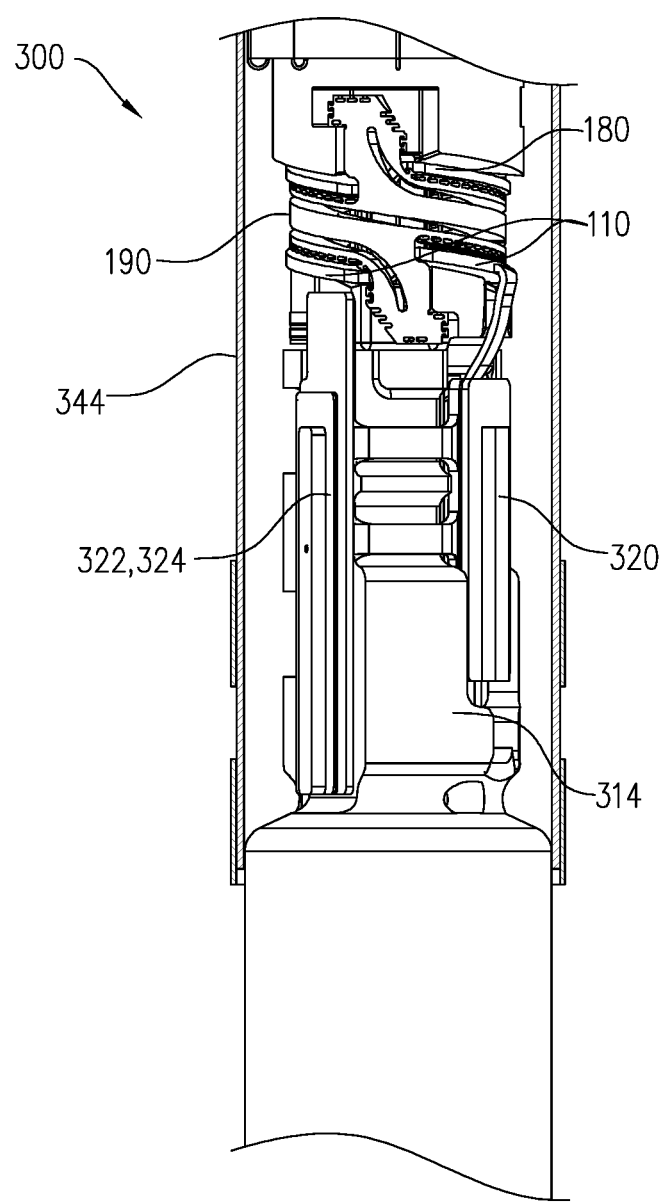
Figure 10D:
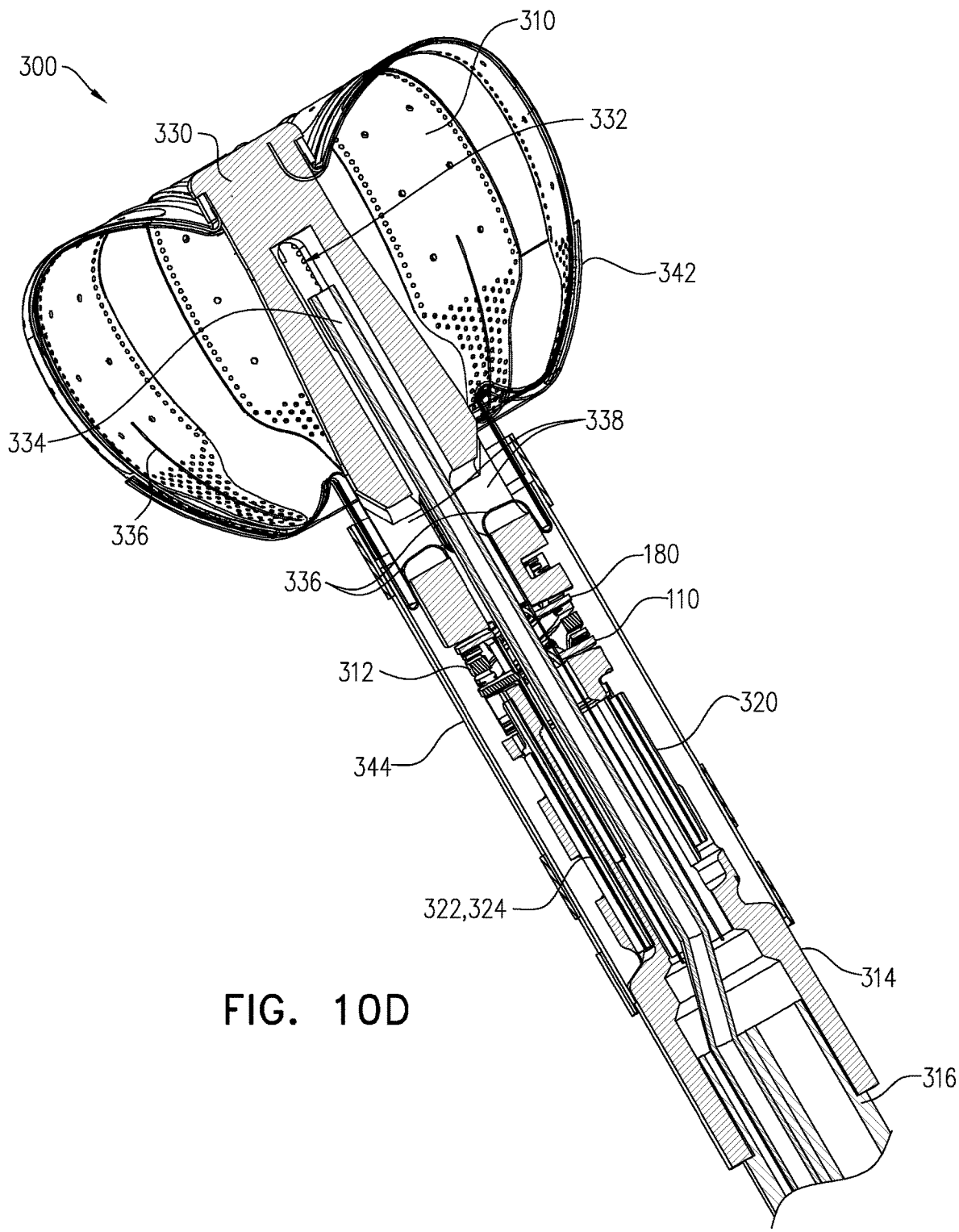

FIGS. 10C and D show a protector sleeve 344 covering the force sensor 312, the x-axis coil 322, the y-axis coil 324 and the solder pad area 320. The protector sleeve 344 is typically formed from any suitable plastic. A deflectable element 346 (in the form of a pull cable) may be disposed in the distal portion of the insertion tube 302 to facilitate deflection of the balloon catheter 300 as shown in FIG. 10D.

Figure 10E:
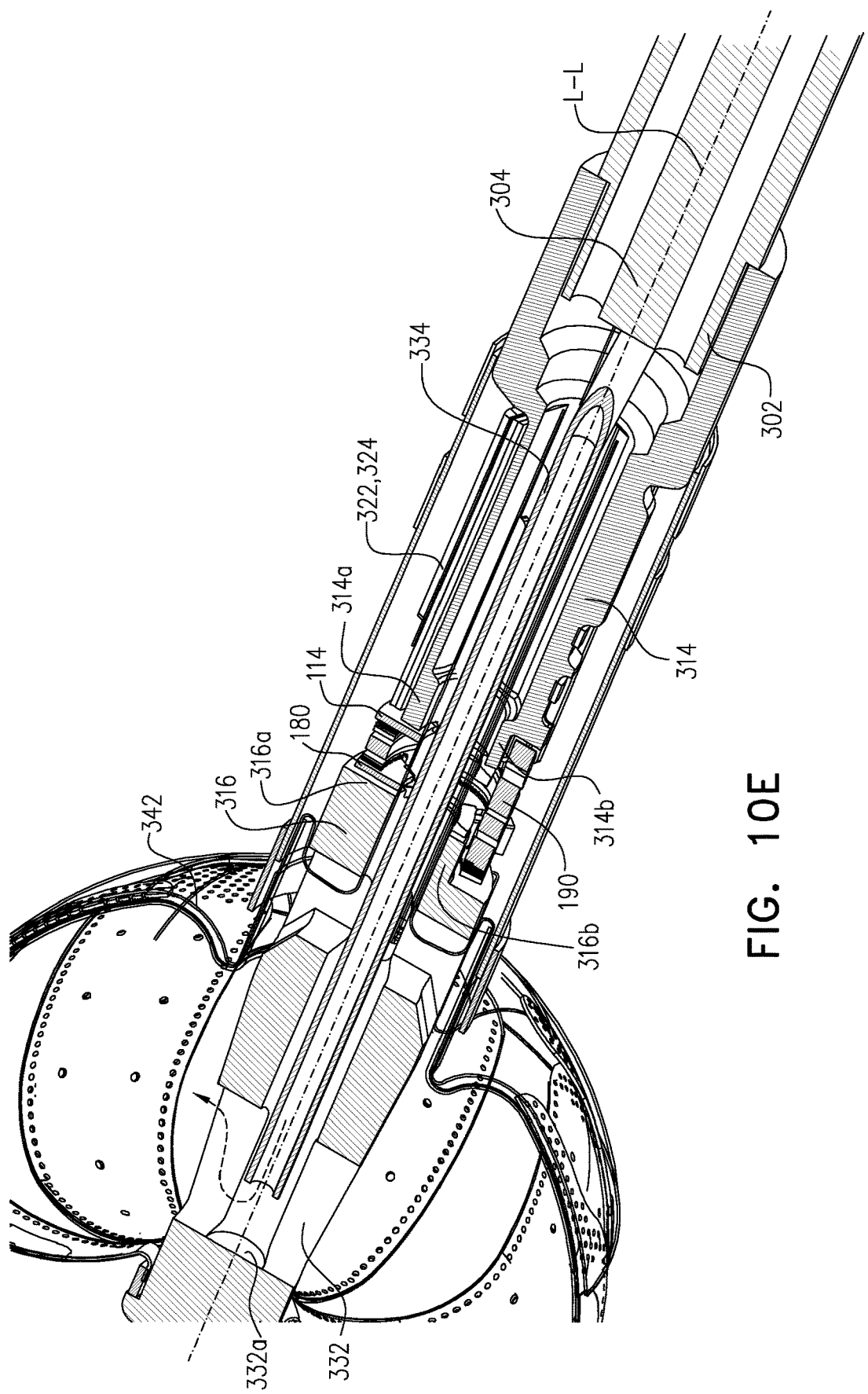
FIG. 10E is a sectional perspective view to show the components inside the catheter of FIG. 9.

FIG. 10E illustrates a sectional view of the exemplary end effector of catheter 24. Starting from distal tip 304 of tubular member 302, a first (or lower) coupler 314 is provided that extends along longitudinal axis L-L of the tubular member 302 through a central opening defined by the location sensor coils 322, 324 and beam coupling member 190 and the contact-force coil circuits 110 and 180. The first coupler 314 terminates just at 314a and 314b before physical contact with the coil 114 (leaving a small gap between the coupler 314 and the coil 114). Coupler 314 is coupled to the beam coupling member 190, shown here in FIG. 10F with other components hidden for clarity. Irrigation fluid (arrow) is delivered along an irrigation tube 334 that extends through coupler 314, beam coupling 190, coupler 316 such that the irrigation fluid impinges against flat surface 332a to redirect fluid flow approximately 90 degrees or more out of ports 332.

Referring to FIG. 10F, which is an exploded view for components discussed in FIG. 10E, coupler 314 is provided with a plurality of notches 314a, 314b, 314c on the periphery of cylindrical member 314 for corresponding engagement with protrusions 194a, 194b, 194c of beam coupling member 190.

A second coupler 316 is provided with notches 316a, 316b, 316c that mates with protrusions 192a, 192b, 192c of beam coupling member 190. Flat surfaces 316d (three shown for coupler 316) are formed whereby each flat surface 316d is angulated with respect to the axis L-L so that each flat surface is complementary to the angulation 190 defined by the helicoid path of ramp 193a, 193b, 193c (i.e., helix angle). Three flat surfaces (not shown due to the perspective view) 314d are also provided for coupler 314 in a configuration similar to flat surface 316d of coupler 316 in that the three flat surfaces 314d are also angulated with respect to the axis L-L so that each flat surface 314d of coupler 314 are generally parallel to the angulation path 190 defined by the helicoid ramp 193a, 193b, 193c as well as flat surface 316d.

The location sensor coils 322 and 324 are mounted to the first coupler 314 in a generally equiangular configuration about the axis L-L. It is noted that while two coils (for XY axes) are used in an exemplary embodiment to determine the location of these coils (as mounted to the coupler and thereby the location of the balloon as the distance between balloon and the location sensor is known), in certain circumstances, only one location sensing coil may be utilized if the other two axes are known via other visualization techniques. As well, three location sensing coils may also be used depending on the packaging constraints of the catheter.

FIG. 10G illustrates the beam coupling member 190 (with other components hidden to better show the structural details). Beam coupling member 190 defines generally a cylindrical form factor about the axis L-L so that beam coupling member 190 can be mounted inside the catheter outer tube 344. Extending along axis L-L to a first (or distal) end in FIG. 10F are three arms 192, each with protrusions 192a, 192b, 192c whereby each protrusion (192a, 192b, or 192c) further extends along a circumferential direction with respect to longitudinal axis L-L. At the other end, extending along axis L-L to a second (or proximal) end in FIG. 10F are three arms 194, each with protrusions 194a, 194b, 194c whereby each protrusion (194a, 194b, or 194c) further extends along a circumferential direction with respect to the longitudinal axis L-L. It is noted that when beam coupling member 190 is viewed with the observer located at the proximal side on axis L-L, protrusions 192a, 192b and 192c extend away from each arm 192 in a counter-clockwise circumferential direction. Contrast this with protrusion 194a, 194b, and 194c (at the other end) which extend away from each arm 194 in a clock-wise circumferential direction. This opposite orientation feature of the protrusions ensures that the couplers 314 and 316 stay connected (via respective notches 314a and 316a) in the catheter once the proximal protrusions (194a, 194b, 194c) of the beam coupling member 190 engages notches (314a, 314b, 314c) of first coupler 314 and the distal protrusions (192a, 192b, 192c) engage with notches (316a, 316b, 316c) of the second coupler 316.

Each protrusion 192a, 192b, 192c is configured to divide into two members so that elements of a biasing or spring member can be formed. For example, protrusion 192a is divided into helicoid ramps 191a and 193a that extend in a circumferential direction with respect to axis L-L and along L-L. Helicoid 191a and 193a defines a spiral-like path around axis L-L and along axis L-L to rejoin at protrusion 194b. As well, protrusion 192b at one end (e.g., distal end) is divided into two helicoid ramps 191b and 193b separated by a through-gap between the two helicoid ramps 191b and 193b and whereby the two ramps 191b and 193b are rejoined at protrusion 194c at the other end (e.g., proximal). Finally, protrusion 192c is divided into ramps 191c and 193c (with a through-gap between them) that spiral around the axis L-L and rejoin at protrusion 194a.

By forming these spiral ramps (with a gap in between each ramp), applicant is able to transform what is essentially a beam-like structure into a hybrid beam-spring coupling with three spiral spring windings. Beyond achieving the function of a coil spring, this design enables applicant to: (a) retain flex circuit 180 between protrusions 192a, 192b, 192c via notches 195; (b) retain flex circuit 110 between protrusions 194a, 194b, 194c via circumferential notches 195; and (c) retain couplers 314 and 316 from separation; and (d) transmit forces to protrusions 192a, 192b, 192c from coupler 316 and transmit forces to protrusions 194a, 194b, 194c from coupler 314 for measurement of the displacement between each of the pie-shaped pair of flex circuits 180 and 110. These features are heretofore not available in this field but for applicant's design described herein.

With this configuration of the couplers 314 and 316 to the beam coupling member 190, forces applied from the balloon 18 to the coupler 316 are transmitted to the beam coupling member 190 such that displacement of discrete portions of beam coupling member 190 can be determined (given that spring constant k of beam coupling member 190 is known prior to installation) by measuring the displacement in the distance "d" between each pair of trefoil force sensor segment in respective flex circuits 180 and 110. Alternatively, after final assembly balloon catheter 300 may be tested to determine constant k, taking into account effects of protector sleeve 344, irrigation line 334, wires 336, and any other components that are functionally in parallel with beam coupling member 190. The results of the testing can be used to calibrate the force sensor to eliminate inaccuracies caused by variations in assembly or manufacturing of components.

As can be seen in FIG. 10F, each of the trefoil force sensor segment 160, 162, 164 for flex circuit 110 is mounted in the beam coupling member 190 such that each segment 160, 162, 164 has a counterpart segment with flex circuit 180. For example, segment 162 of flex circuit 110 is mounted to be parallel to segment 182 of flex circuit 180 at a specified distance "d" (which distance "d" can change when forces are applied to coupler 316 or 314). The remainder of the force sensor coil segments 162 and 164 of flex circuit 110 are mounted in a similar manner with the respective trefoil force sensor segment of flex circuit 180. Displacement for each pair of trefoil force sensor segment will allow console 24 to determine the angle and direction of forces being applied to which one of the pie-shaped force sensor coil segment pairs. For example, when distance "d" (opposite facing arrows in FIG. 10F) between force sensor coil segments 162 and 182 is changed without the distance on the other two pair of force sensor coil segments being changed, then the processor of the system is able to determine that a force is being applied along one of the directions designated by the dual-facing arrow (FIG. 10F).

Figure 11:
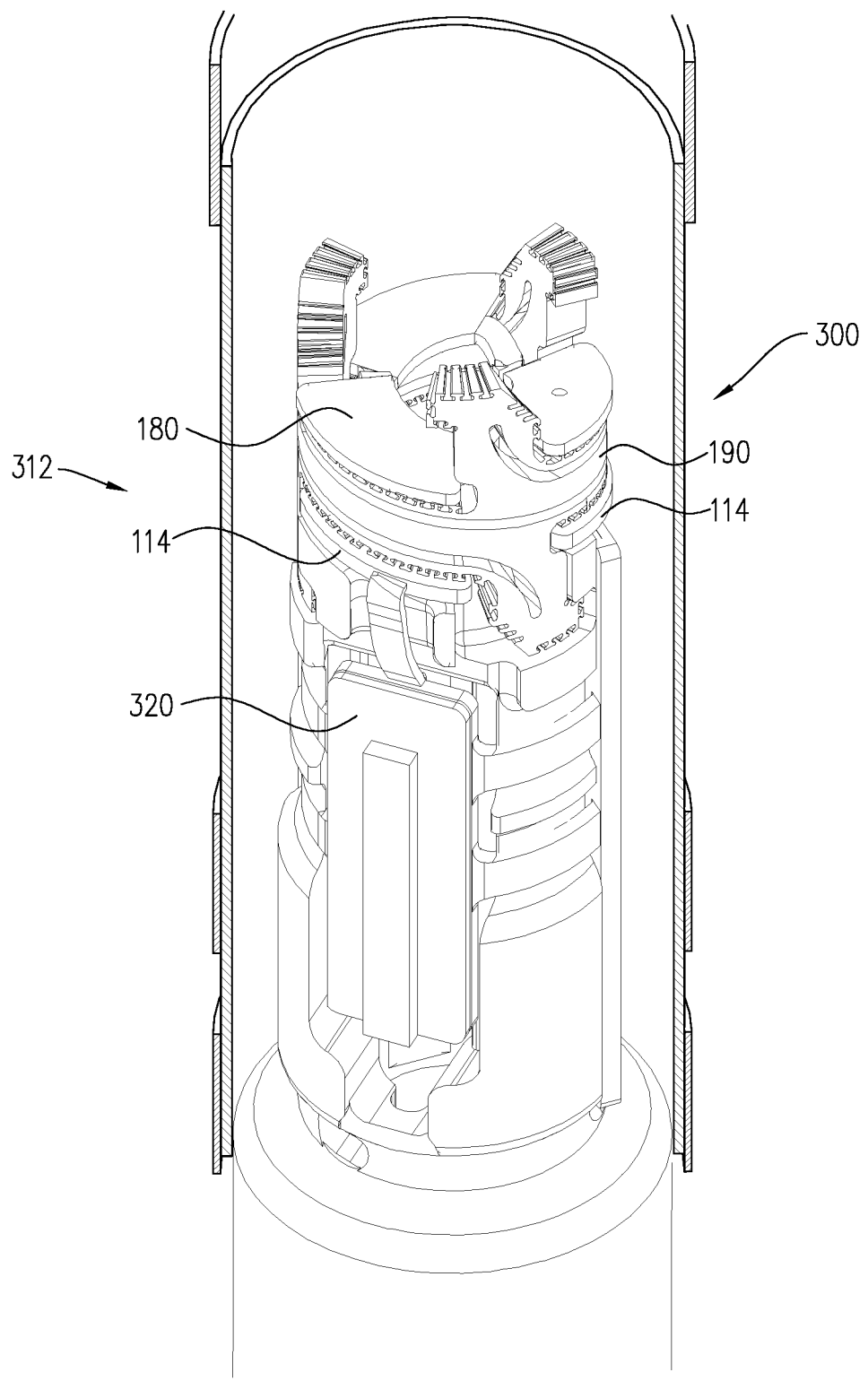
FIGS. 11 and 12 are semi-transparent views of sensors of the balloon catheter of FIG. 9.
Figure 12:
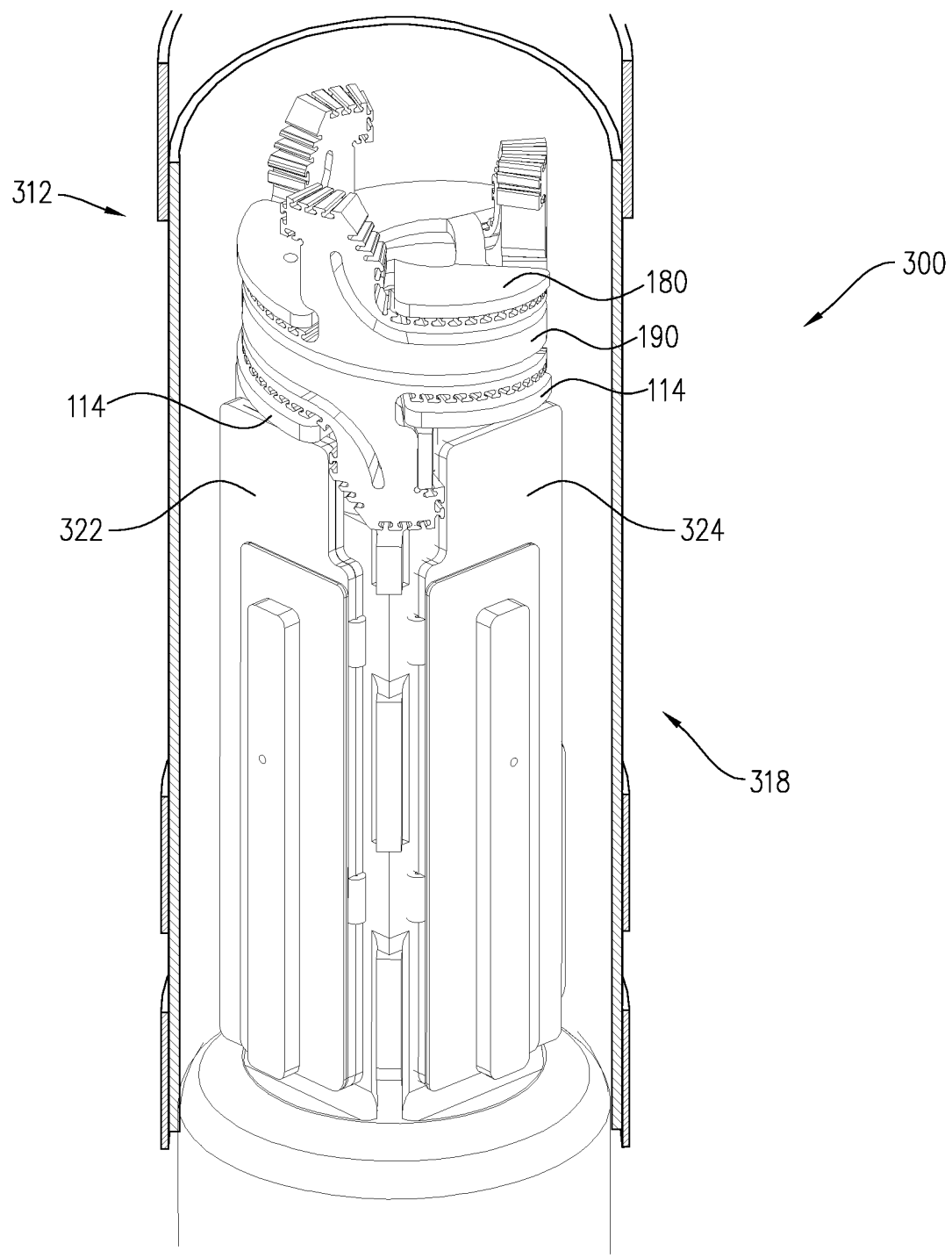

Reference is now made to FIGS. 11 and 12, which are semi-transparent views of sensors of the balloon catheter 300 of FIG. 9. The force sensor 312 is comprised of the beam coupling member 190 with the first portion 114 of flexible circuit 110 (FIG. 3) disposed on bottom face of the beam coupling member 190, and the flexible circuit 180 disposed on the top face of the beam coupling member 190. In some embodiments, the first portion 114 is disposed on top face, and the flexible circuit 180 is disposed on the bottom face. The various components of the beam coupling member 190, and the flexible circuits 110, 180 have been described in detail with reference to FIGS. 2-8.

FIG. 11 shows a solder pad area 320 which includes a plurality of solder pads (e.g., about eleven), which may include the solder joints 168 of portion 142 (FIG. 2) for connecting the coils of the flexible circuit 110 (FIG. 3) and optionally the coil(s) of the flexible circuit 180 to the console 24 (FIG. 1). FIG. 12 shows an x-axis coil 322 and a y-axis coil 324 forming part of the position sensor 318. The x-axis coil 322 and the y-axis coil 324 may be formed from the segments 122, 124, 132, and 134, described above with reference to FIGS. 2 and 3 in more detail.

Figure 13:
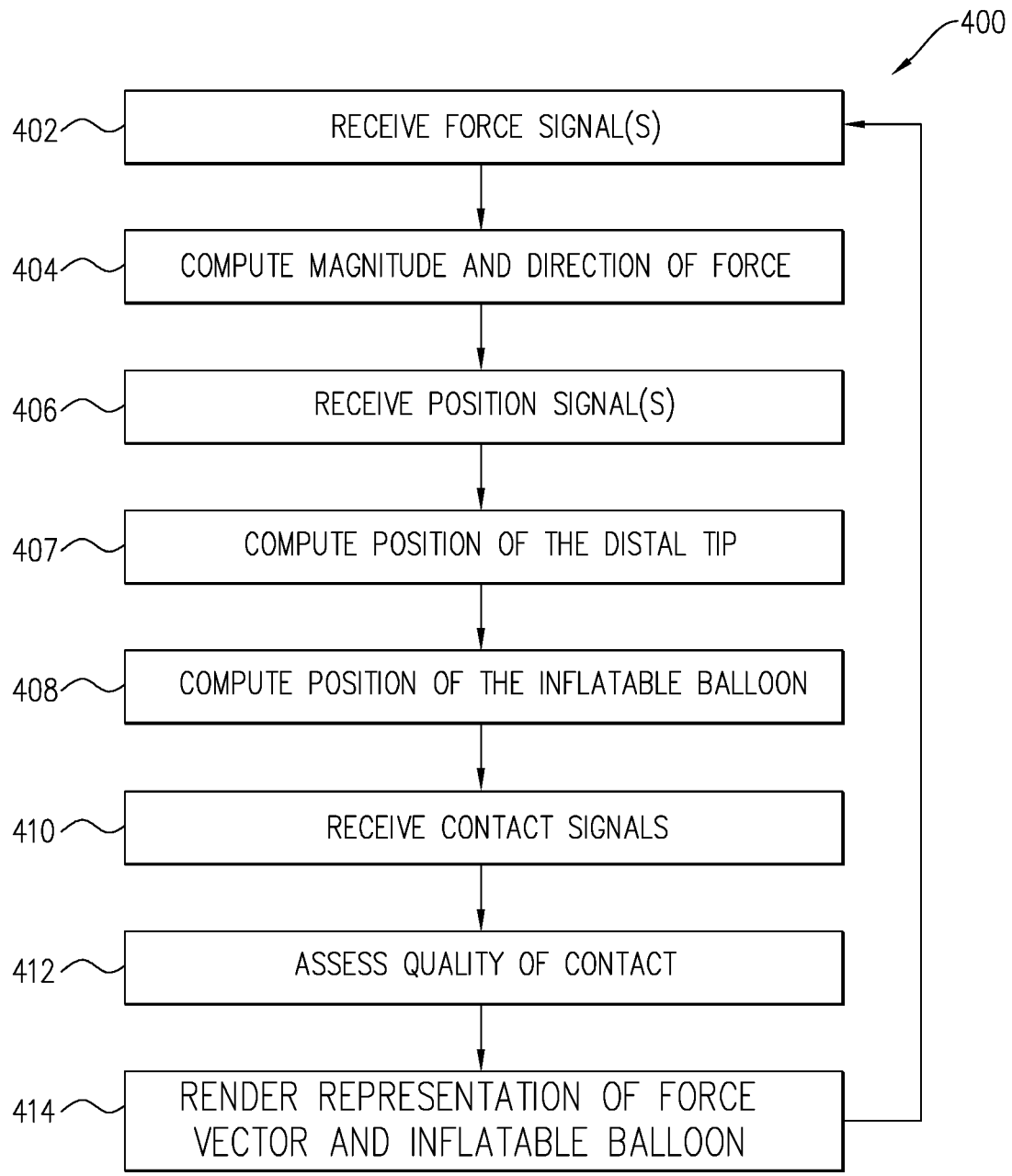
FIG. 13 is a flowchart including steps in a method of operation of the system of FIG. 1 using the balloon catheter of FIG. 9.

Reference is now made to FIG. 13, which is a flowchart 400 including steps in a method of operation of the system 10 of FIG. 1 using the balloon catheter 300 of FIG. 9. The steps described below do not need to be performed in the order described. The steps may be performed in any suitable order. Some of the steps may be performed in parallel to each other.

The processor 22 (FIG. 1) is configured to receive (block 402) force signal(s) from the force sensor 312 (FIGS. 9-12). The processor 22 (FIG. 1) is configured to compute (block 404) a magnitude and direction of a force measured by the force sensor 312 responsively to the force signal(s).

The force sensor 312 may be calibrated using any suitable method. In accordance with some embodiments, the distal tip 304 is held in a clamp or other apparatus, while the inflatable balloon 306 is deflected using a robot. The robot measures the lateral and angular displacement of the inflatable balloon 306 with respect to the distal tip 304, and the corresponding force applied on the inflatable balloon 306 by the robot using a strain gauge, as well as the corresponding force signal(s) provided by the force sensor 312. The robot may also perform the above measurements while applying the force from different directions around the axis of the inflatable balloon 306. The calibration measurements may then be stored in a table, or the like, for future lookup. Therefore, in use of the system 10, the magnitude and direction of the force applied by the inflatable balloon 306 may be computed from force signal(s) output by the force sensor 312 by looking up corresponding values in the table and by performing appropriate interpolation or extrapolation of the values found in the table. The force signal(s) are also indicative of a lateral and angular displacement of the inflatable balloon 306 with respect to the distal tip 304 and may therefore be used to determine the lateral and angular displacement of the inflatable balloon 306 with respect to the distal tip 304 and therefore the position (location and orientation) of the inflatable balloon 306 (described in more detail below).

The processor 22 (FIG. 1) is configured to receive (block 406) position signal(s) from the position sensor 318 (FIGS. 9, 10, 12) and/or the electrodes 310 (FIGS. 9 and 10). The processor 22 (FIG. 1) is configured to compute (block 407) the position of the distal tip 304 responsively to the position signal(s). The processor 22 is configured to compute (block 408) a position (location and orientation) of the inflatable balloon responsively to the computed position of the distal tip 304 and the force signal(s) (which yields the lateral and angular displacement of the inflatable balloon 306 with respect to the distal tip 304).

The processor 22 (FIG. 1) is configured to receive (block 410) contact signals from the electrodes 310 (FIGS. 9 and 10). The processor 22 (FIG. 1) is configured in response to the contact signals, to assess (block 412) a respective quality of contact of each of the electrodes 310 with the tissue.

Figure 14:
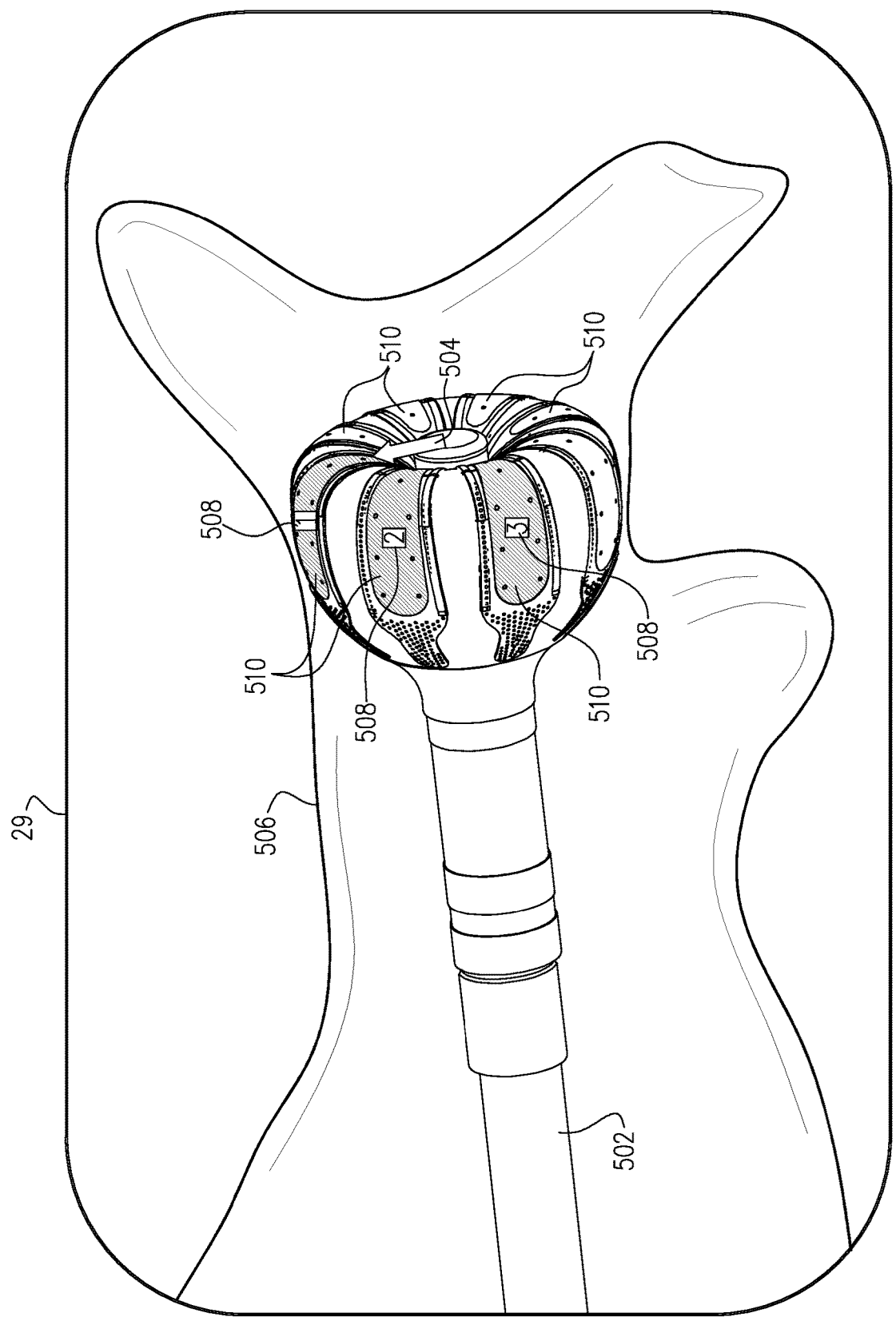
FIG. 14 is a schematic view of rendering a representation of the balloon catheter of FIG. 9 and a force vector.

Reference is now made to FIG. 14, which is a schematic view of rendering a representation 502 of the balloon catheter 300 of FIG. 9 and a representation 504 of a force vector. Reference is also made to FIG. 13.

The processor 22 (FIG. 1) is configured to render (block 414) to the display 29 the representation 504 of the force vector responsively to the computed magnitude and direction, and the representation 502 of the inflatable balloon 306 (FIG. 9) responsively to the computed position of the inflatable balloon 306 (which is based on the computed position of the distal tip 304 and the force signal(s), as described above with the step of block 408 of FIG. 13), while modifying a visual feature of one(s) of the electrodes 310 (FIG. 9) responsively to the respective quality of contact of the electrodes 310 with the tissue at the respective locations. The electrodes 310 having a quality of contact above a given quality of contact are highlighted as compared to other electrodes 310. The electrode representations in FIG. 14 are labeled with reference numeral 510. The highlighted electrodes may be displayed in a different color and/or using a greater brightness and/or using a border or any suitable way to distinguish the electrodes 310 having the quality of contact above the given quality of contact as compared to other electrodes 310. The electrodes 310 may be labeled using electrode numbers 508 to allow the operator 16 to easily identify which electrodes are in contact with the tissue. In FIG. 14, the highlighted electrodes include the electrode numbers 508, while non-highlighted electrodes do not include the electrode numbers 508. In some embodiments, both highlighted and non-highlighted electrodes may be numbered. The representation 502 of the balloon catheter 300 and the representation 504 of the force vector may also be displayed with an image 506 of the body-part in which the balloon catheter 300 is inserted. The image 506 of the body-part may be acquired from a CT or MRI scan, or any suitable scan, which has been preregistered with the system 10 (FIG. 1). The steps 402-414 may be performed in any suitable order and may be repeated intermittently or periodically so as to update the position of the balloon catheter 300 with respect to the body-part and/or the size and magnitude of the force vector.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A system comprising a balloon catheter configured to be inserted into a body-part of a living subject, the balloon catheter comprising:
  an insertion tube comprising a distal tip;
  a force sensor disposed distal to the distal tip, the force sensor comprising a spring member comprising:
    at least one distal arm extending to a distal end of the force sensor along a longitudinal axis;
    at least one distal coupling protrusion disposed at the distal end of the force sensor and extending away from the at least one distal arm in a first circumferential direction about the longitudinal axis;
    at least one proximal arm extending to a proximal end of the force sensor along the longitudinal axis and away from the at least one distal arm;
    at least one proximal coupling protrusion disposed at the proximal end of the force sensor extending away from the at least one proximal arm in a second, opposite circumferential direction relative to the at least one distal coupling protrusion and about the longitudinal axis such that the at least one distal coupling protrusion and the proximal coupling protrusion have an opposite circumferential orientation relative to one another; and
    a first helicoid ramp and a second helicoid ramp separated by a through-gap between the first and second helicoid ramps, the first and second helicoid ramps each comprising:
      a first section that extends along the spring member at a helix angle; and
      a second section extending from the first section that curves, relative to the helix angle, towards the at least one distal coupling protrusion and onto the at least one distal arm,
    the first and second helicoid ramps joining at a distal end of the second sections;
  an inflatable balloon including:
    a proximal portion connected to the force sensor via the distal coupling protrusion so that the force sensor is disposed between the distal tip of the insertion tube and the inflatable balloon; and
    multiple electrodes disposed around an outer surface of the inflatable balloon, and configured, when the inflatable balloon is inflated, to contact tissue at respective locations in the body-part; and
  a coupler attached to the distal tip of the insertion tube and to the force sensor via the at least one proximal coupling protrusion, the force sensor being configured to output at least one force signal indicative of a magnitude and a direction of a force applied by the inflatable balloon on the tissue when the inflatable balloon is inflated.

2. The system according to claim 1, further comprising:
a display; and
processing circuitry configured to:
compute the magnitude and the direction of the force responsively to the at least one force signal; and
render to the display a representation of a force vector and a representation of the inflatable balloon, responsively to the at least one force signal.

3. The system according to claim 2, wherein:
the balloon catheter further comprises at least one position sensor configured to output at least one position signal indicative of a position of the distal tip;
the processing circuitry is configured to:
compute the position of the distal tip responsively to the at least one position signal; and
render to the display the representation of the force vector responsively to the computed magnitude and direction, and the representation of the inflatable balloon responsively to the computed position and the at least one force signal.

4. The system according to claim 2, wherein the processing circuitry is configured to:
receive a plurality of contact signals from the multiple electrodes;
in response to the plurality of contact signals, assess a respective quality of contact of each of the multiple electrodes with the tissue; and
render to the display the representation of the inflatable balloon, while modifying a visual feature of one of the multiple electrodes responsively to the respective quality of contact of the multiple electrodes with the tissue at the respective locations.

5. The system according to claim 2, wherein the processing circuitry is further configured to:
compute a location of the distal tip responsive to receiving at least one location signal from at least one location sensing coil;
receive a plurality of contact signals from the multiple electrodes; and
determine a respective quality of contact of each of the multiple electrodes with the tissue based at least in part on the plurality of contact signals and the at least one force signal.

6. The system according to claim 5, wherein the processing circuitry is further configured to:
render to the display the representation of the inflatable balloon and the representation of the force vector responsive to the computed magnitude and direction, while modifying a visual feature of at least one of the multiple electrodes based at least in part on the respective quality of contact of the multiple electrodes with the tissue at the respective locations and the at least one force signal.

7. The system according to claim 2, wherein:
the balloon catheter further comprises at least one impedance-based position sensor configured to output at least one position signal indicative of a position of the distal tip; and
the processing circuitry is further configured to:
compute the position of the distal tip responsively to the at least one position signal;
receive a plurality of contact signals from the multiple electrodes;
in response to the plurality of contact signals and the at least one force signal, assess a respective quality of contact of each of the multiple electrodes with the tissue;
render to the display the representation of the inflatable balloon responsive to the computed magnitude and direction and the computed position; and
render to the display the representation of the force vector responsively to the computed magnitude and direction, while modifying a visual feature of at least one of the multiple electrodes based at least in part on the respective quality of contact of the multiple electrodes with the tissue at the respective locations and the at least one force signal.

8. The system according to claim 7, wherein the processing circuitry is further configured to render to the display the representation of the force vector and the representation of the balloon catheter with an image of the body-part, the image of the body-part being taken from an anatomical scan.

9. The system according to claim 1, wherein each of the multiple electrodes is a flexible electrode formed from a polyamide substrate with a gold covering thereon.

10. The system according to claim 1, the coupler comprising at least one notch, the at least one proximal coupling protrusion mating with the at least one notch.

11. The system according to claim 1, wherein the coupler is a first coupler, and the system comprises a second coupler attached to the inflatable balloon and comprising at least one notch, the at least one distal coupling protrusion mating with the at least one notch of the second coupler.

12. The system according to claim 1, wherein the first and second helicoid ramps extend in a spiral direction along the longitudinal axis towards the at least one proximal coupling protrusion.

13. The system according to claim 1, further comprising a flex circuit comprising two location sensing coils.

14. The system according to claim 1, wherein the multiple electrodes comprise at least one ablation electrode mounted on the inflatable balloon and at least one temperature sensor mounted on the inflatable balloon.

15. The system according to claim 14, wherein the at least one ablation electrode comprises eight ablation electrodes and the at least one temperature sensor comprises eight temperature sensors.

16. The system according to claim 1, further comprising a flex circuit disposed at least partially on the coupler, the flex circuit having at least one location sensing coil.

17. The system according to claim 16, the at least one distal arm comprising a notch that retains the flex circuit.

18. The system according to claim 1, wherein the first and second helicoid ramps each comprise:
a third section extending from the first section that curves, relative to the helix angle, towards the at least one proximal coupling protrusion and onto the at least one proximal arm,
the first and second helicoid ramps joining at a distal end of the third sections.

19. A system comprising a balloon catheter configured to be inserted into a body-part of a living subject, the balloon catheter comprising:
an insertion tube comprising a distal tip;
a force sensor disposed distal to the distal tip, the force sensor comprising a spring member comprising:
at least one distal arm extending to a distal end of the force sensor along a longitudinal axis;

at least one distal coupling protrusion disposed at the distal end of the force sensor and extending away from the at least one distal arm;

at least one proximal arm extending to a proximal end of the force sensor along the longitudinal axis and away from the at least one distal arm;

at least one proximal coupling protrusion disposed at the proximal end of the force sensor extending away from the at least one proximal arm; and a first helicoid ramp and a second helicoid ramp separated by a through-gap between the first and second helicoid ramps, the first and second helicoid ramps each comprising:
- a first section that extends along the spring member at a helix angle;
- a second section extending from the first section that curves, relative to the helix angle, towards the at least one distal coupling protrusion and onto the at least one distal arm, the first and second helicoid ramps joining at a distal end of the second sections; and
- a third section extending from the first section that curves, relative to the helix angle, towards the at least one proximal coupling protrusion and onto the at least one proximal arm, the first and second helicoid ramps joining at a distal end of the third sections; and an inflatable balloon comprising:
- a proximal portion connected to the force sensor via the distal coupling protrusion so that the force sensor is disposed between the distal tip of the insertion tube and the inflatable balloon; and
- multiple electrodes disposed around an outer surface of the inflatable balloon, and configured, when the inflatable balloon is inflated, to contact tissue at respective locations in the body-part, the force sensor being configured to output at least one force signal indicative of a magnitude and a direction of a force applied by the inflatable balloon on the tissue when the inflatable balloon is inflated.

* * * * *